(12) United States Patent
Ribault et al.

(10) Patent No.: US 8,815,173 B2
(45) Date of Patent: Aug. 26, 2014

(54) DECONTAMINATION METHOD AND SYSTEM IMPLEMENTING IT

(75) Inventors: Sebastien Ribault, Romanswiller (FR); Christel Noehringer, Colmar (FR); Vincent Kieffer, Otterswiller (FR)

(73) Assignee: EMD Millipore Corporation, Billerica, MA (US)

( * ) Notice: Subject to any disclaimer, the term of this patent is extended or adjusted under 35 U.S.C. 154(b) by 0 days.

(21) Appl. No.: 13/101,408

(22) Filed: May 5, 2011

(65) Prior Publication Data

US 2011/0206559 A1    Aug. 25, 2011

Related U.S. Application Data

(62) Division of application No. 12/287,613, filed on Oct. 10, 2008.

(30) Foreign Application Priority Data

Oct. 17, 2007  (FR) ...................................... 07 58400

(51) Int. Cl.
*A61L 2/00* (2006.01)
*A61L 2/20* (2006.01)
*A61L 2/24* (2006.01)
*G01N 35/02* (2006.01)
*G01N 35/00* (2006.01)

(52) U.S. Cl.
CPC ....... *A61L 2/208* (2013.01); *G01N 2035/00277* (2013.01); *A61L 2/24* (2013.01); *G01N 35/02* (2013.01)
USPC .......................................... 422/300; 422/305

(58) Field of Classification Search
USPC .......... 422/291, 292, 297–300, 305, 307, 308
See application file for complete search history.

(56) References Cited

U.S. PATENT DOCUMENTS

| 3,728,227 A | 4/1973 | Elson et al. |
| 4,089,989 A | 5/1978 | White et al. |

(Continued)

FOREIGN PATENT DOCUMENTS

| EP | 0299517 A2 | 1/1989 |
| EP | 0350271 A2 | 1/1990 |

(Continued)

OTHER PUBLICATIONS

European Communication dated Feb. 23, 2009 in corresponding foreign patent application No. EP 08290970.6-2113.

(Continued)

*Primary Examiner* — Timothy Cleveland
(74) *Attorney, Agent, or Firm* — Nields, Lemack & Frame, LLC

(57) ABSTRACT

The method of microbiological decontamination of a machine comprising an enclosure (5, 100) for treating a support (6) and a conveyor comprising a shuttle (30), comprises the steps of obtaining a container (6) adapted to be received on said shuttle (30) and to diffuse biocidal agent in said enclosure (5, 100), of placing said container (6) on said shuttle (30), of moving said shuttle (30) within said enclosure, and of evacuating said agent. The microbiological analysis system comprises a container (6), a microbiological analysis machine comprising at least two stations (2, 3, 4) for treatment of said support (6), a conveyor comprising a shuttle (30) adapted to receive and to move said support (6), said container (6) being adapted to be received on said shuttle (30), as well as means (150, 156, 159) for evacuating said biocidal agent.

5 Claims, 22 Drawing Sheets

(56) References Cited

U.S. PATENT DOCUMENTS

| | | |
|---|---|---|
| 4,116,631 A | 9/1978 | Trinel et al. |
| 4,169,123 A | 9/1979 | Moore et al. |
| 4,280,624 A | 7/1981 | Ford |
| 4,551,133 A | 11/1985 | Zegers de Beyl et al. |
| 4,614,300 A | 9/1986 | Falcoff |
| 4,681,740 A | 7/1987 | Commarmot et al. |
| 4,707,334 A | 11/1987 | Gerhard |
| 4,978,335 A | 12/1990 | Arthur, III |
| 4,984,490 A | 1/1991 | Kurki |
| 5,180,606 A | 1/1993 | Stokes et al. |
| 5,232,664 A | 8/1993 | Krawzak et al. |
| 5,448,499 A | 9/1995 | Palmer |
| 5,782,897 A | 7/1998 | Carr |
| 6,199,766 B1 | 3/2001 | Fox et al. |
| 7,013,202 B2 | 3/2006 | Farina et al. |
| 8,071,022 B2 | 12/2011 | Ribault et al. |
| 2002/0027135 A1 | 3/2002 | Fagrell et al. |
| 2002/0072122 A1 | 6/2002 | Copeland et al. |
| 2002/0101310 A1 | 8/2002 | Jennings |
| 2002/0114733 A1 | 8/2002 | Copeland et al. |
| 2004/0009098 A1 | 1/2004 | Torre-Bueno |
| 2004/0197230 A1 | 10/2004 | Lemme et al. |
| 2004/0200227 A1 | 10/2004 | Melching et al. |
| 2004/0265447 A1 | 12/2004 | Raniwala |
| 2005/0013737 A1 | 1/2005 | Chow et al. |
| 2005/0042710 A1 | 2/2005 | Oshima et al. |
| 2005/0135972 A1 | 6/2005 | Lemme et al. |
| 2005/0153453 A1 | 7/2005 | Copeland et al. |
| 2006/0051243 A1 | 3/2006 | Chow et al. |
| 2006/0151185 A1 | 7/2006 | Takagi et al. |
| 2007/0231844 A1 | 10/2007 | Grinon et al. |
| 2008/0147056 A1 | 6/2008 | van der Weide et al. |

FOREIGN PATENT DOCUMENTS

| | | |
|---|---|---|
| EP | 0974827 A2 | 1/2000 |
| EP | 1515100 A1 | 3/2005 |
| EP | 1826276 A1 | 8/2007 |
| EP | 1826548 A1 | 8/2007 |
| FR | 2341649 A1 | 9/1977 |
| FR | 2677273 A1 | 12/1992 |
| FR | 2897873 A1 | 8/2007 |
| WO | 94/19922 A2 | 9/1994 |
| WO | 97/13136 A1 | 4/1997 |
| WO | 02/091134 A2 | 11/2002 |
| WO | 2007/069005 A1 | 6/2007 |

OTHER PUBLICATIONS

French Search Report dated Jul. 4, 2008 in corresponding foreign patent application No. FR 0758400.

French Search Report dated Apr. 14, 2008 in co-pending foreign patent application No. Fr 0758395.

French Search Report dated Apr. 16, 2008 in co-pending foreign patent application No. FR 0758398.

French Search Report dated Apr. 15, 2008 in co-pending foreign patent application No. FR 00758397.

French Search Report dated Jul. 18, 2008 in co-pending foreign patent application No. FR 0758399.

Office Action dated Jul. 6, 2010 in co-pending foreign U.S. Appl. No. 12/287,609.

Office Action dated Jan. 24, 2011 in corresponding U.S. Appl. No. 12/287,613.

Office Action dated May 25, 2011 in corresponding U.S. Appl. No. 12/287,613.

Office Action dated May 9, 2011 in co-pending U.S. Appl. No. 12/287,576.

Office Action dated Dec. 22, 2010 in co-pending U.S. Appl. No. 12/287,574.

Office Action dated Apr. 1, 2011 in co-pending U.S. Appl. No. 12/287,614.

Notice of Allowance mailed Sep. 12, 2011 in corresponding U.S. Appl. No. 12/287,613.

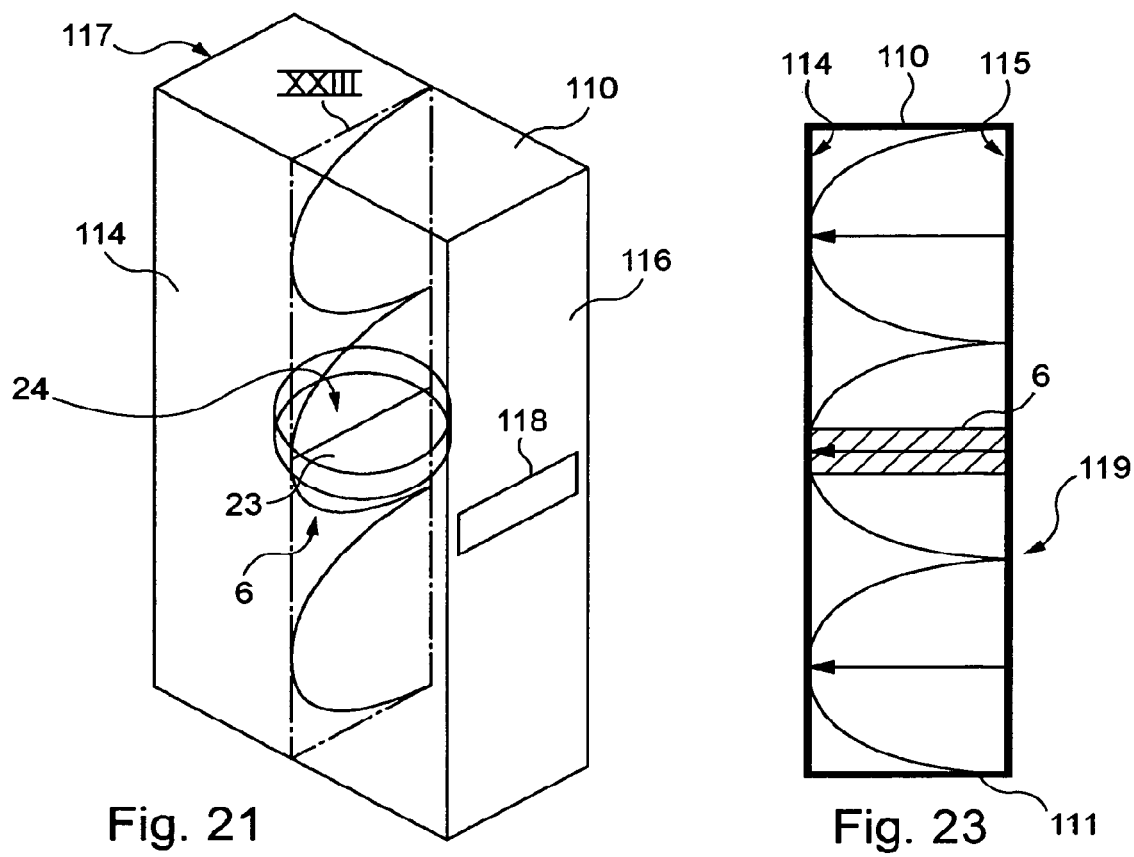
Fig. 21
Fig. 23
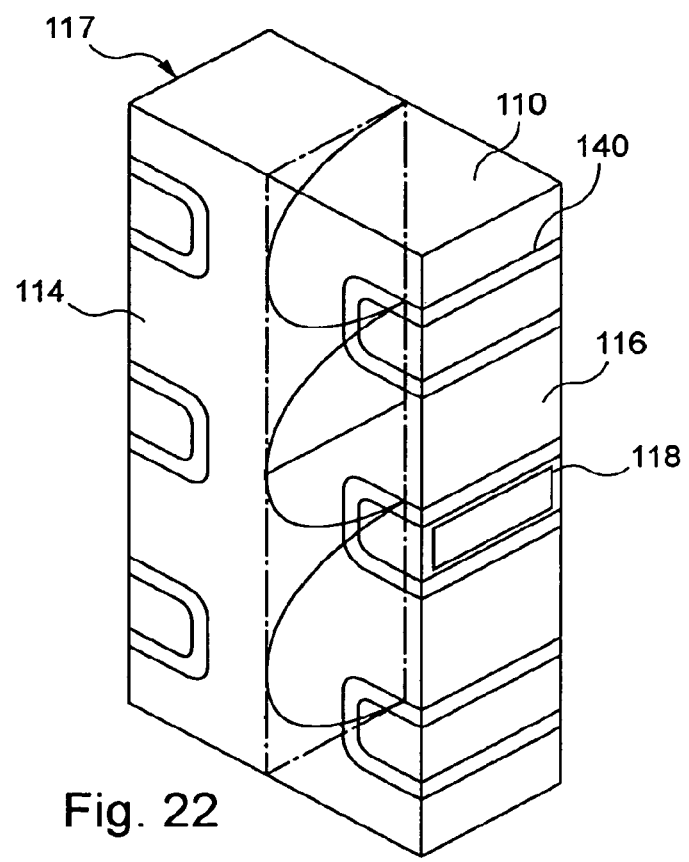
Fig. 22

DECONTAMINATION METHOD AND SYSTEM IMPLEMENTING IT

This application is a divisional of U.S. patent application Ser. No. 12/287,613 filed Oct. 10, 2008, which claims priority of French Patent Application No. 0758400 filed Oct. 17, 2007, the disclosures of which are incorporated herein by reference.

The present invention concerns the microbiological decontamination of enclosures.

It is known that it is important to be able to decontaminate enclosures in order to inactivate the microorganisms that they may contain.

This is in particular of the utmost importance for enclosures of microbiological analysis machines which must be able to be decontaminated very regularly in order to avoid any risk of contamination of the supports to analyze by microorganisms that may possibly be present in the analysis enclosure (risk of detection of false positives).

Traditionally a method of decontamination consists of spreading a biocidal agent in the zone to decontaminate in order for it to act and inactivate the germs that may possibly be present then to evacuate the biocidal agent.

The invention concerns providing a method of the same type that is both convenient and simple to implement.

To that end it provides a method of microbiological decontamination of a machine comprising an enclosure for treating a support to analyze and a conveyor comprising a shuttle for moving said support within said enclosure in order for it to be treated by successive treatment stations of said machine, characterized in that it comprises the steps of:

obtaining a container adapted to be received on said shuttle and to diffuse biocidal agent in said enclosure;

placing said container on said shuttle;

moving said shuttle within said enclosure between said stations; and evacuating said agent.

In the method according to the invention and by virtue of the use of the conveyor, it is thus possible to have the biocidal agent spread efficiently in all the regions of the enclosure, the biocidal agent being diffused in the whole space by virtue of the movement of the shuttle in the enclosure.

The method according to the invention thus makes it possible to efficiently dispense with all particular means for enabling efficient decontamination such as the addition of inlet pipes for the biocidal agent at several locations of the enclosure in order to ensure a homogenous diffusion of that agent in the enclosure.

According to preferred features, for reasons of simplicity and convenience for both manufacture and use, the step of placing said container on said shuttle is implemented by disposing said container at the intended location on said shuttle to receive a support to analyze.

The location provided on the shuttle for receiving a support in order to place there the container diffusing the biocidal agent is thus taken advantage of, this making it possible in particular to have a twin function shuttle without however having to re-dimension it.

According to still other features preferred for the same reasons as those set forth above, the method comprises, prior to the step of placing said container on said shuttle, the step of selecting, as said container, a support that is identical to those intended to be analyzed.

The use of a support initially intended for analysis thus makes it possible to take advantage of supports that already exist to transform them into containers diffusing the biocidal agent such that it is thus not necessary to design a specific container.

According to still other preferred features, the method comprises the step of selecting, as said conveyor, a conveyor of which the shuttle is adapted to receive a support comprising a membrane and a tubular body surrounding said membrane.

The membrane is particularly well-adapted since on account of its absorbent capacities it is perfectly capable of absorbing a liquid which may be a precursor agent of the diffused biocidal agent.

According to still other preferred features, the method comprises, prior to the step of placing said container on said shuttle, the step of depositing in said container a precursor agent of the biocidal agent and, between the step of placing said container on said shuttle and the step of moving said shuttle within said enclosure between said stations, the step of activating said precursor agent.

According to still other preferred features, said step of activating said precursor agent is implemented by a step of heating said precursor agent.

This heating step may thus in particular be implemented by a heating station sometimes originally present on certain machines to perform for example the lysis of the microorganisms, such that it is not necessary to provide an additional station on those machines to activate the precursor agent.

According to still other preferred features:

the heating is heating by microwaves; and/or the method comprises the step of selecting hydrogen peroxide in liquid phase as said precursor agent.

According to a second aspect the invention also concerns a system for microbiological analysis of a support appropriate for the implementation of the method as set forth above, characterized in that it comprises:

a container adapted to diffuse a biocidal agent.

a machine for microbiological analysis comprising a treatment enclosure adapted to receive a said support, at least two stations for treating said support, a conveyor comprising a shuttle adapted to receive and to move said support between said stations, said container being adapted to be received on said shuttle, as well as means for evacuating said biocidal agent.

According to features that are preferred for reasons of simplicity and convenience for both manufacture and use:

The system also comprises a precursor agent of said biocidal agent to deposit on said container and to activate to diffuse said biocidal agent, said machine also comprising means for activating said precursor agent;

said activating means comprise a station for heating said container; and/or the heating station comprises a microwave cavity and a magnetron.

The features and advantages of the invention will appear from the following description, given by way of preferred but non-limiting example, with reference to the accompanying drawings in which.

Figure 5:
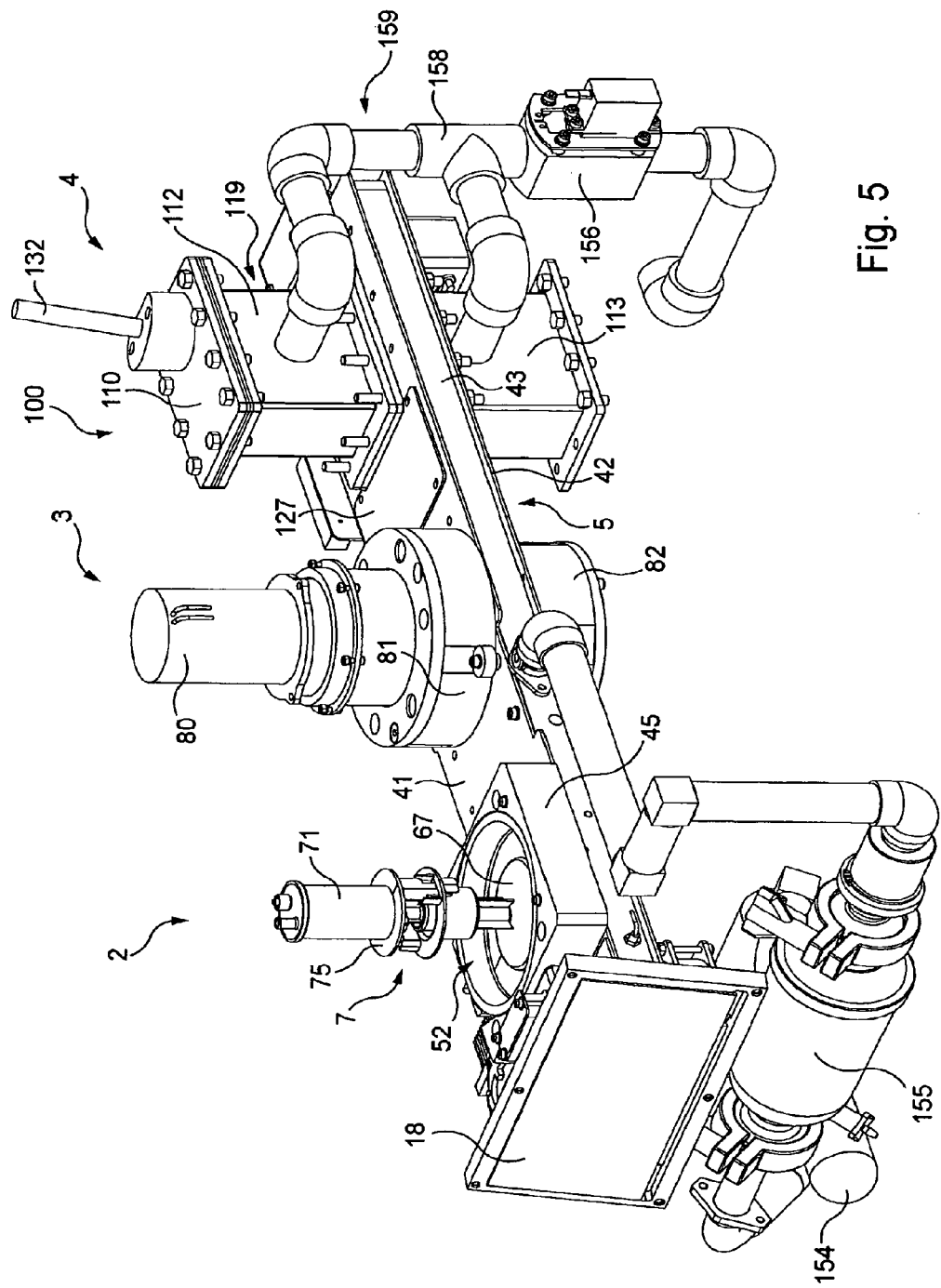
Figure 6:
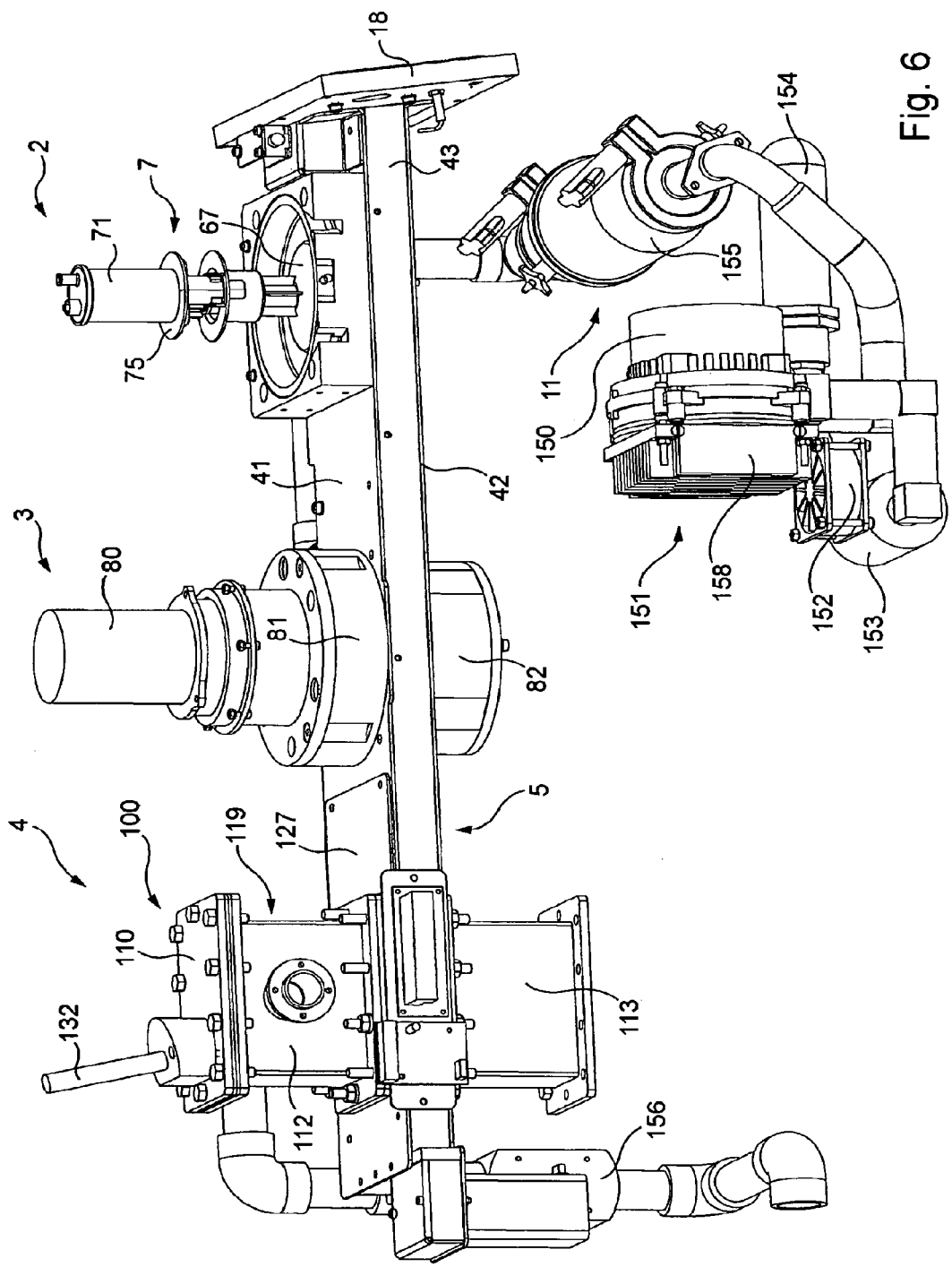
Figure 7:
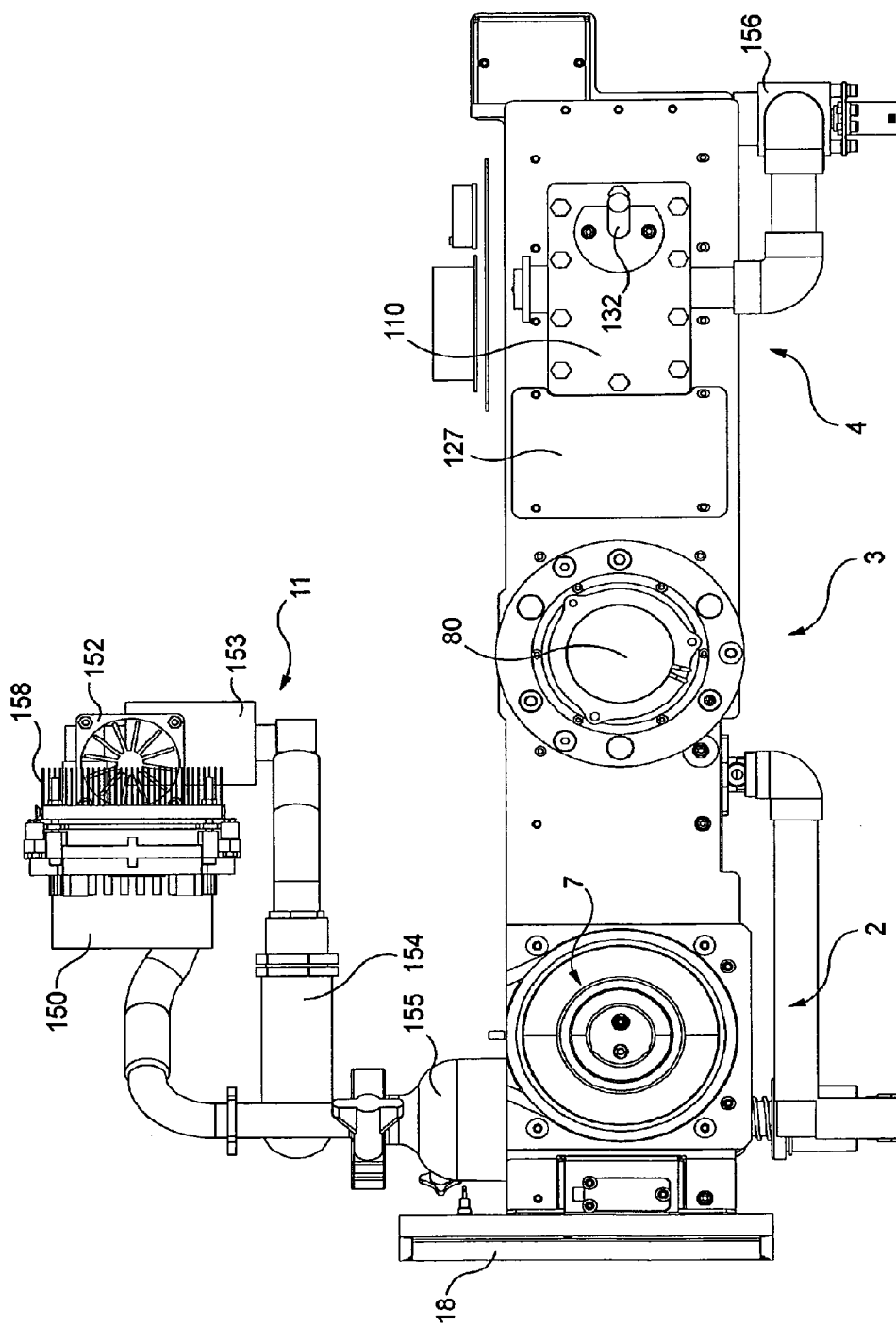
Figure 8:
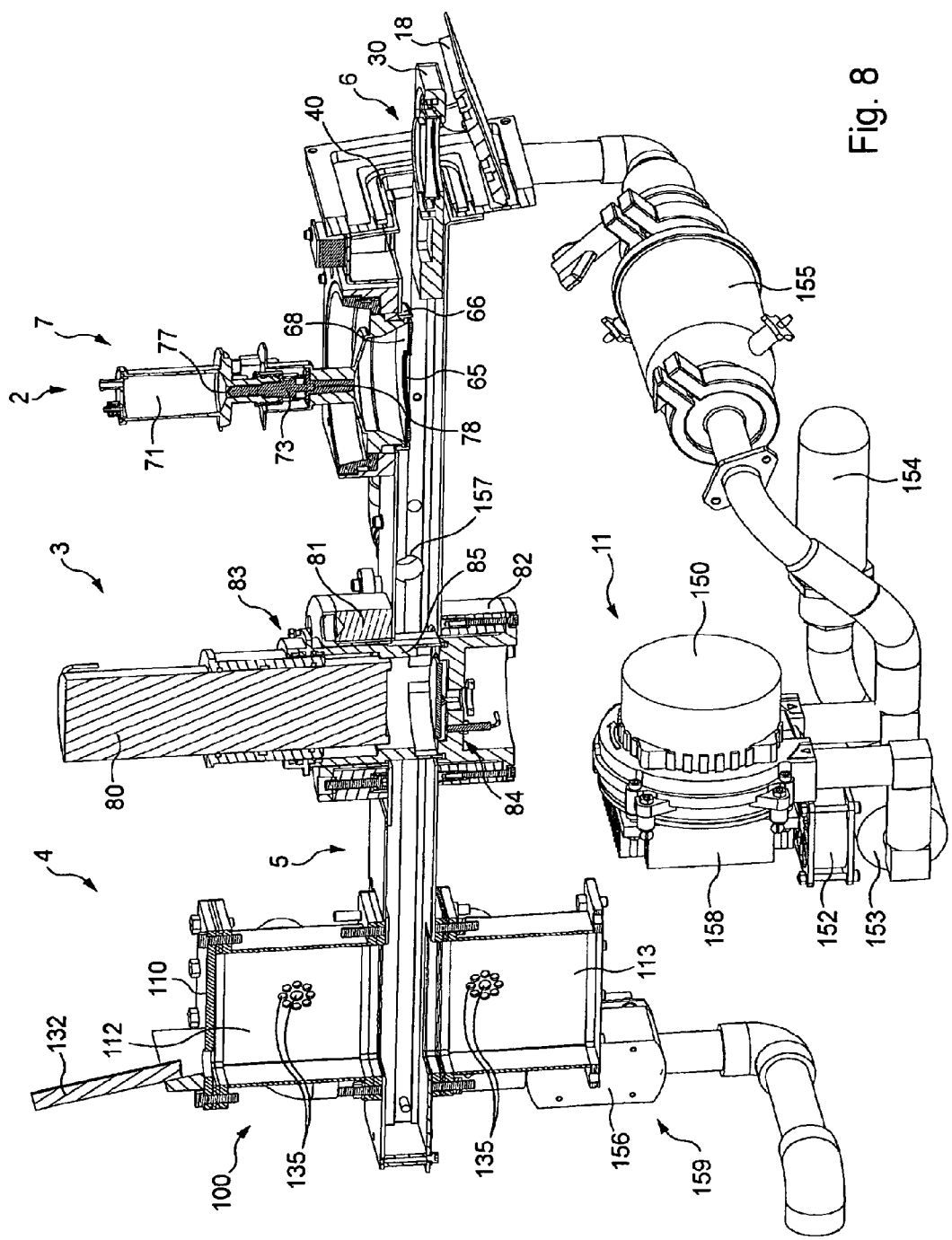
Figure 9:
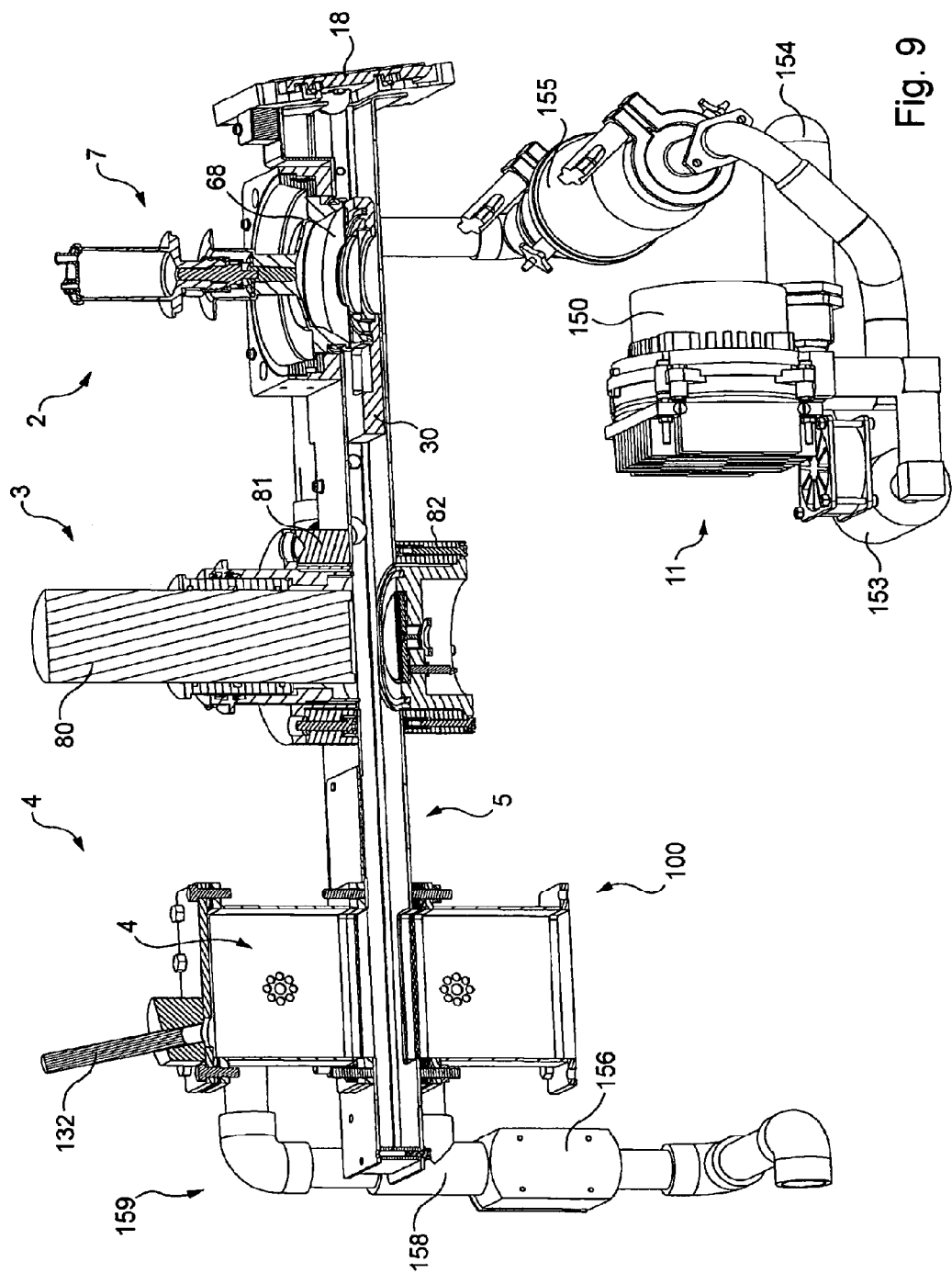

FIGS. 5, 6 and 7 are respectively two views in perspective taken from two different angles and a plan view taken from above showing a conveyor duct of the machine in isolation, in which the shuttle transporting a filter unit to analyze moves, a pneumatic circuit associated with that conveyor duct and, from left to right in FIG. 5, a spraying station on that unit, a station for measuring the luminance emitted by that unit and a station for heating that unit;

FIGS. 8 to 11 are four views similar to FIG. 6 but taken in perspective-section along a median plane of symmetry of the duct and respectively illustrating the shuttle a position for receiving the filter unit to analyze where it projects from the conduit by a passage window, in a spraying position in which it is situated under a spraying device received in a receptacle for receiving the spraying station, in a measuring position in which it is situated under a photomultiplier of the luminance measuring station, and in a heating position in which it is situated in the microwave cavity of the heating station.

Figure 2:
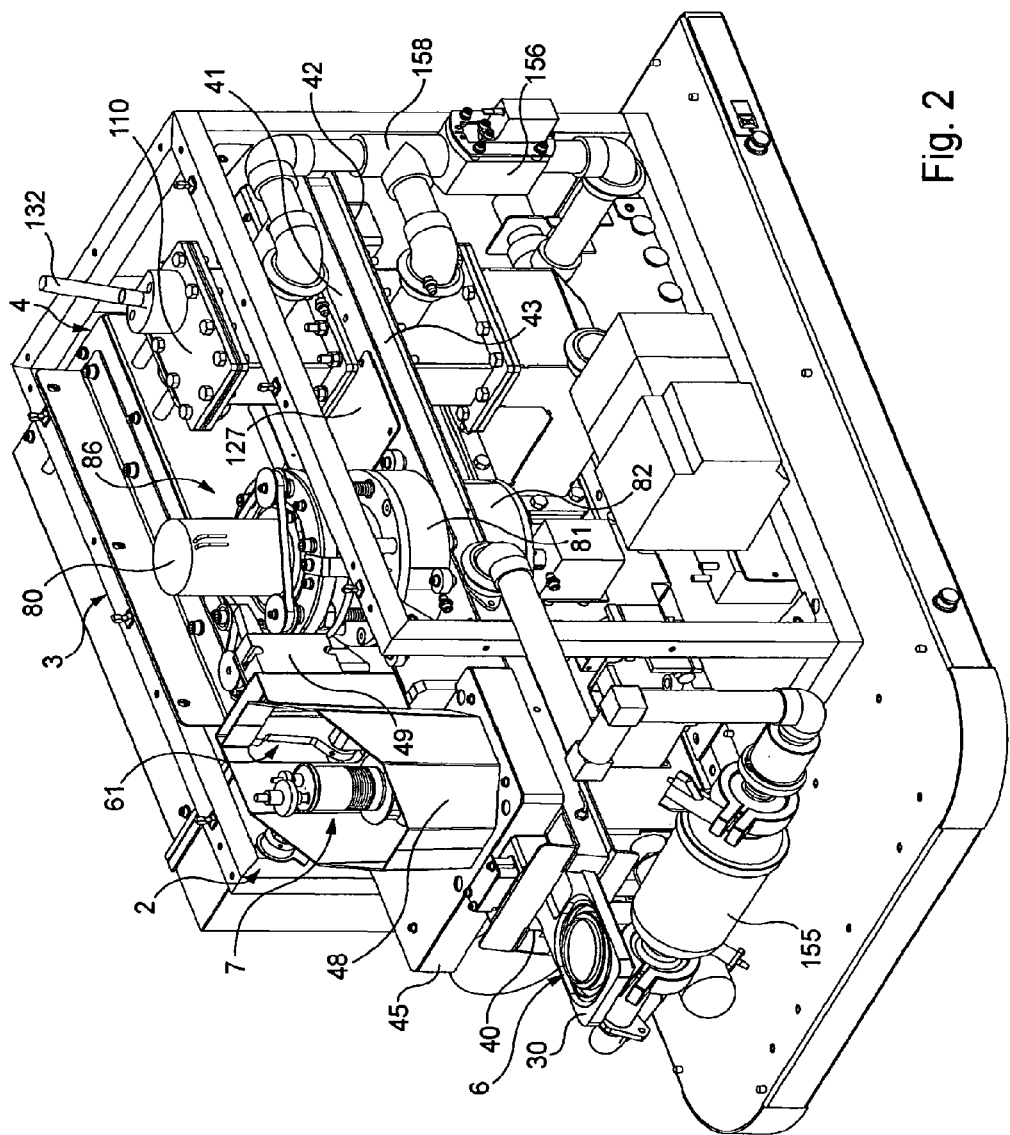
FIG. 2 is a view similar to FIG. 1 but in which the protective cover of the machine is not represented.
Figure 3:
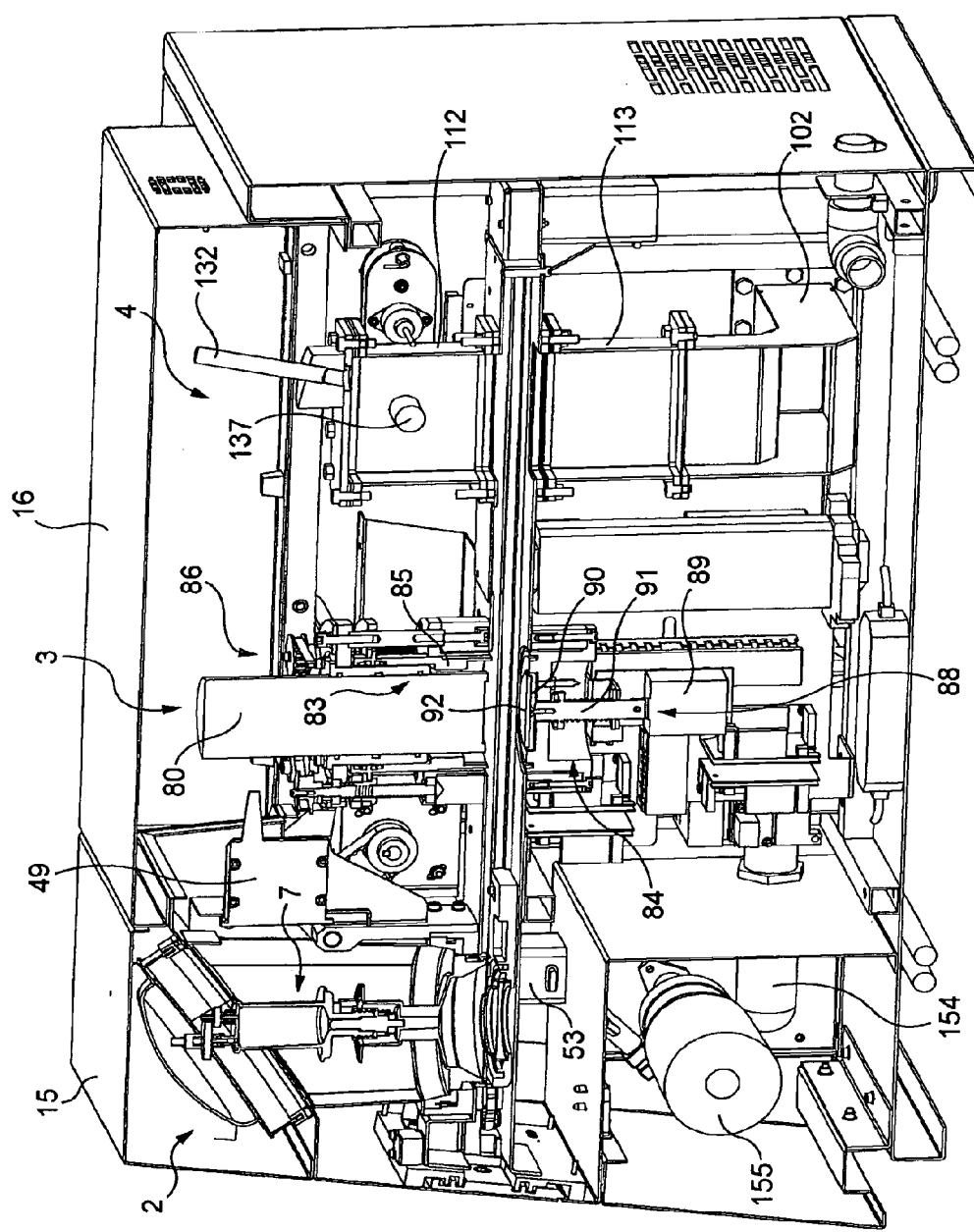
FIG. 3 is a perspective-section view of that machine taken on a vertical plane centered on the path of a shuttle of a conveyor of the machine.
Figure 4:
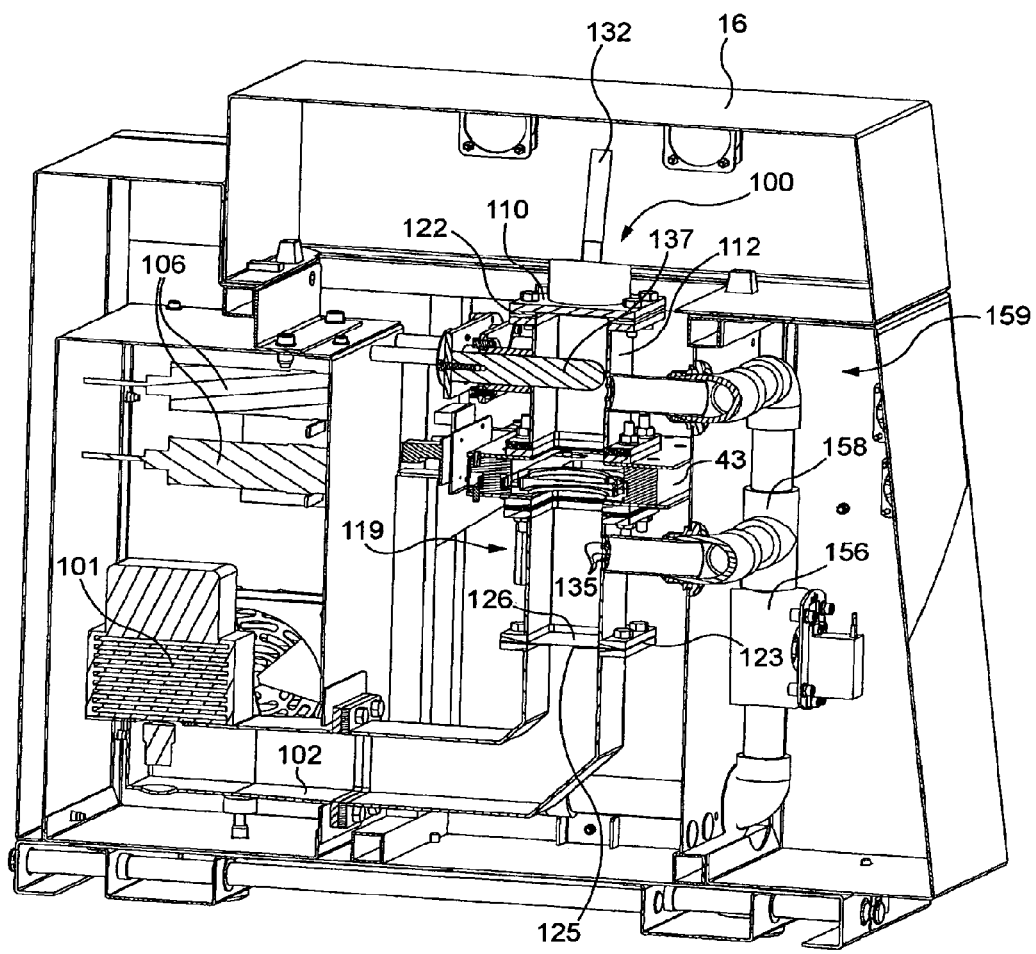
FIG. 4 is a view similar to FIG. 3 but taken on a section plane transverse to the section plane of FIG. 3, corresponding to a median plane of symmetry of a microwave cavity of the machine.
Figure 10:
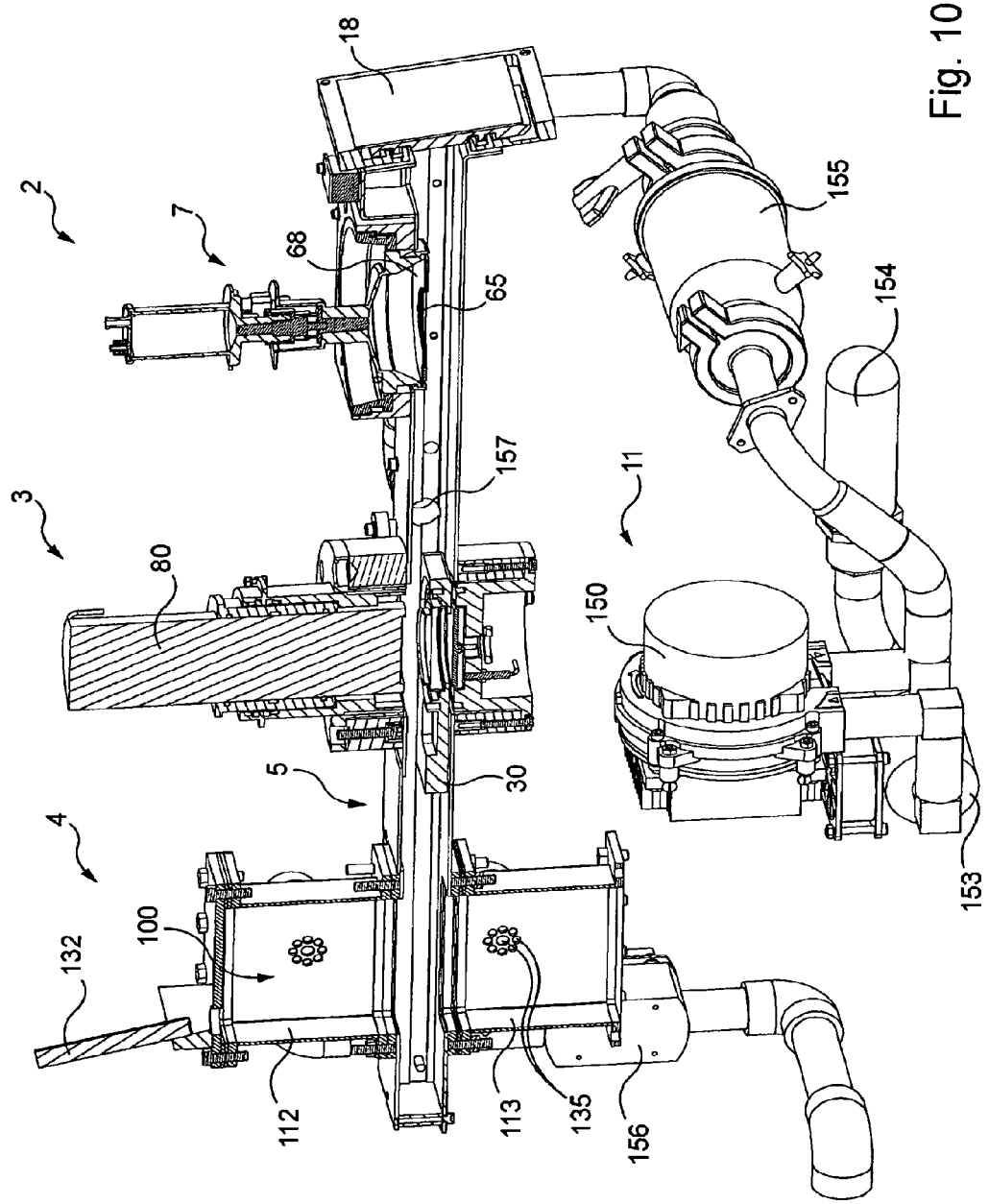
Figure 12:
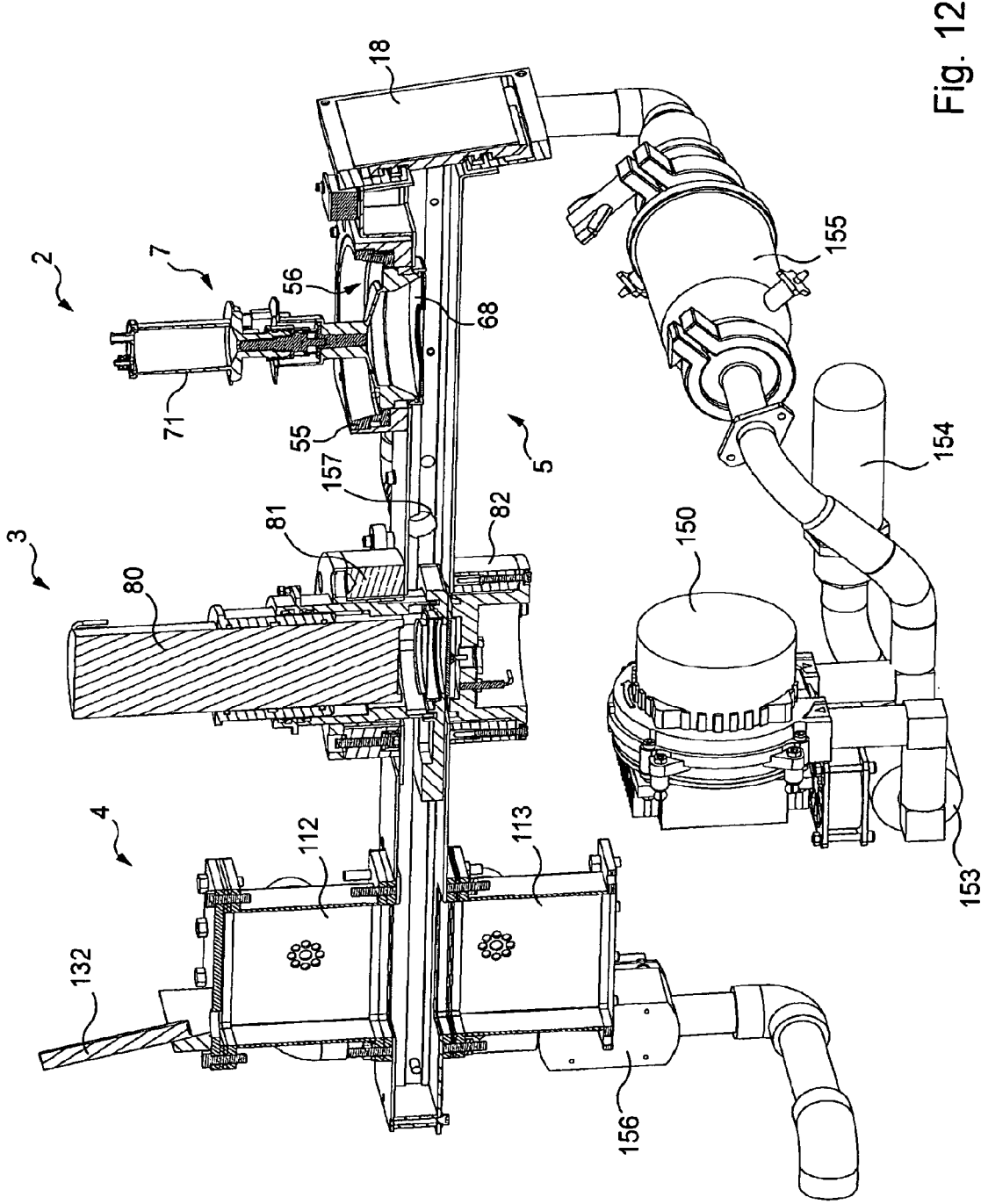
Figure 13:
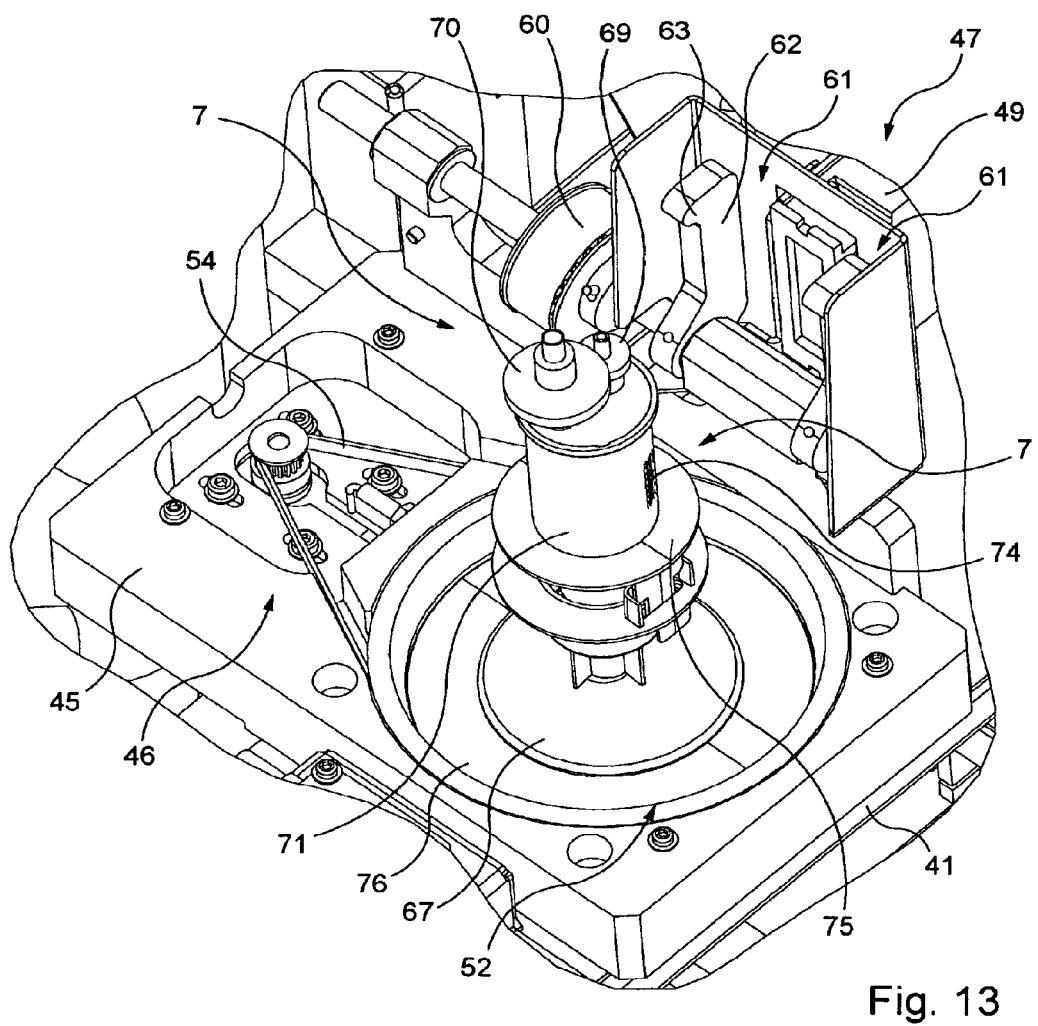
Figure 14:
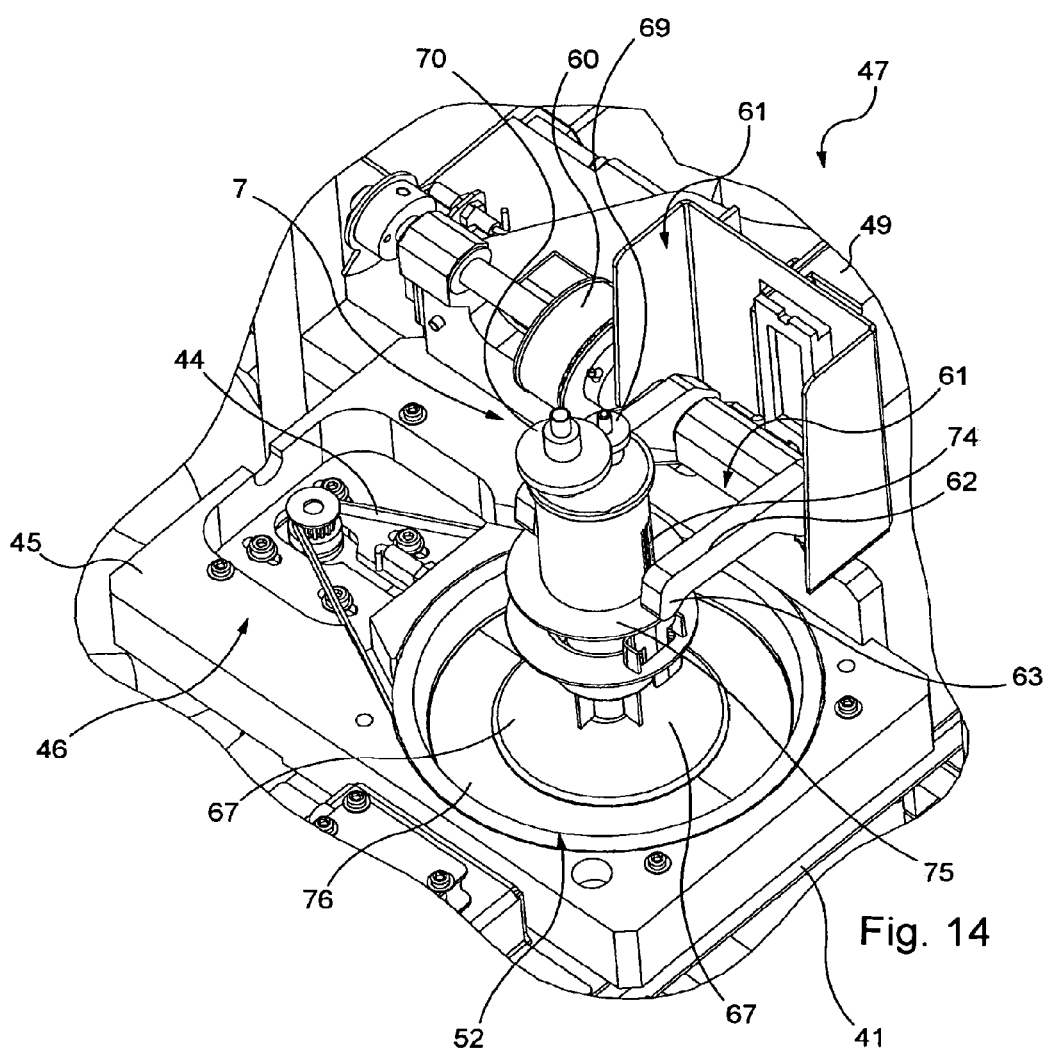
Figure 15:
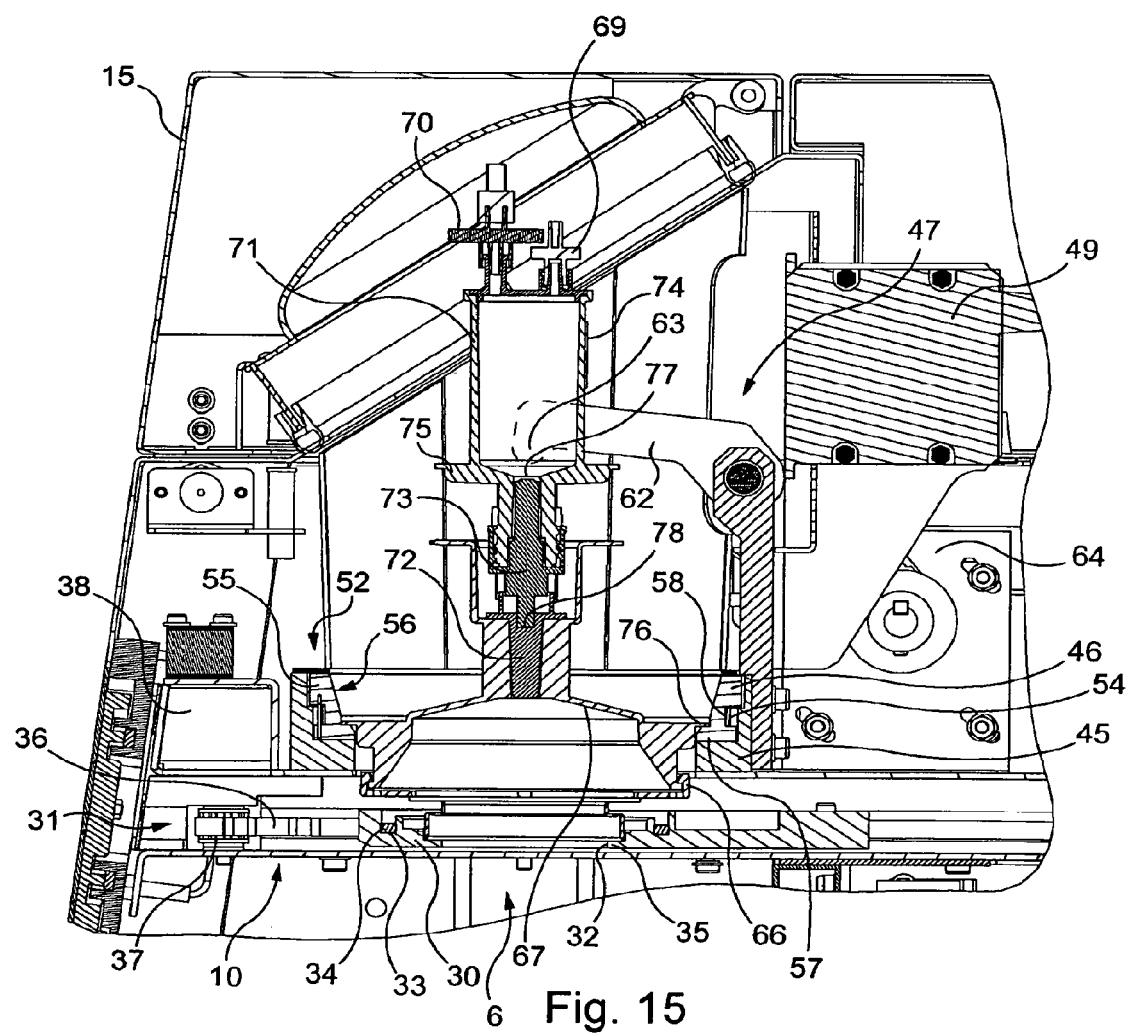
Figure 16:
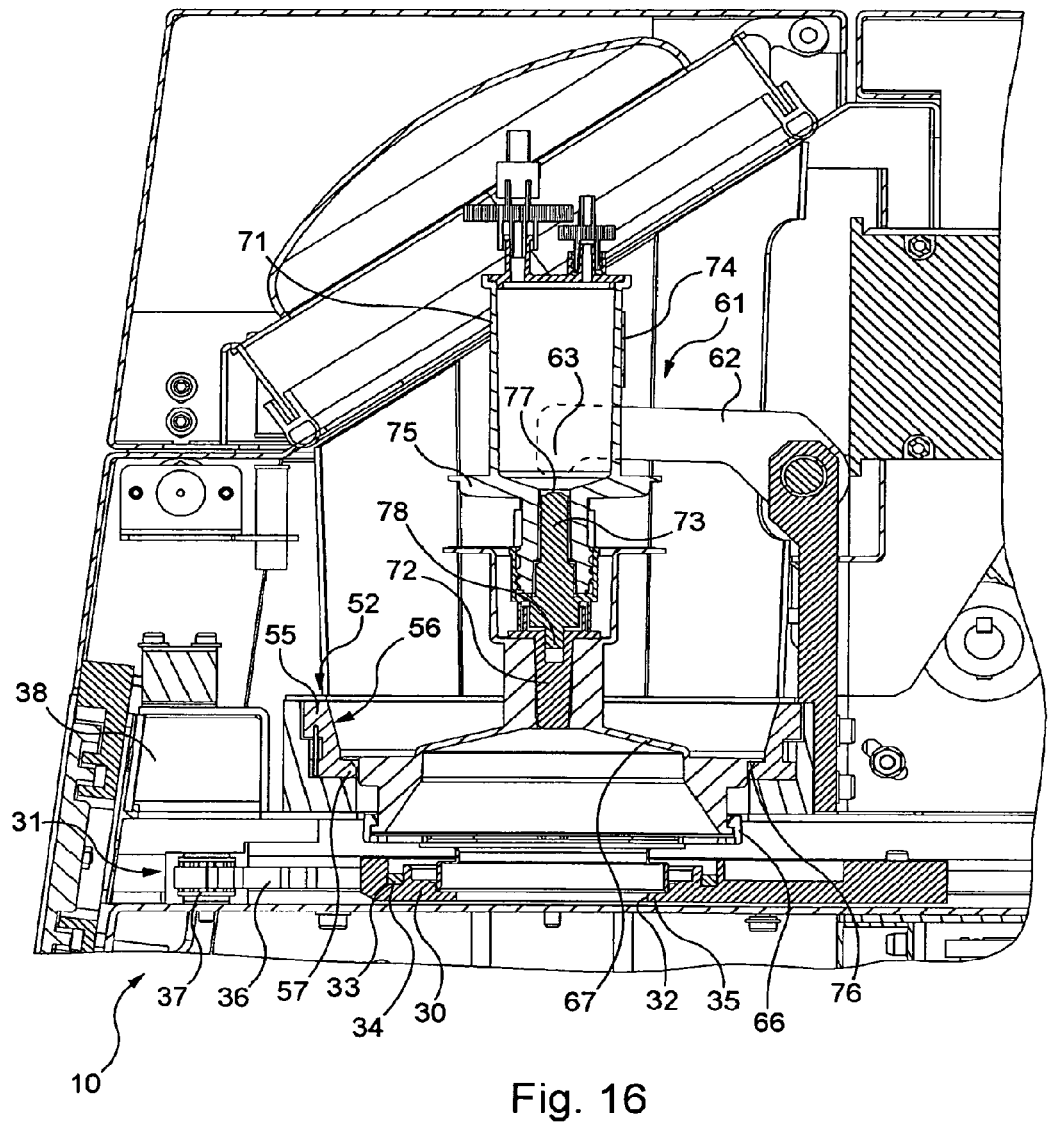
Figure 17:
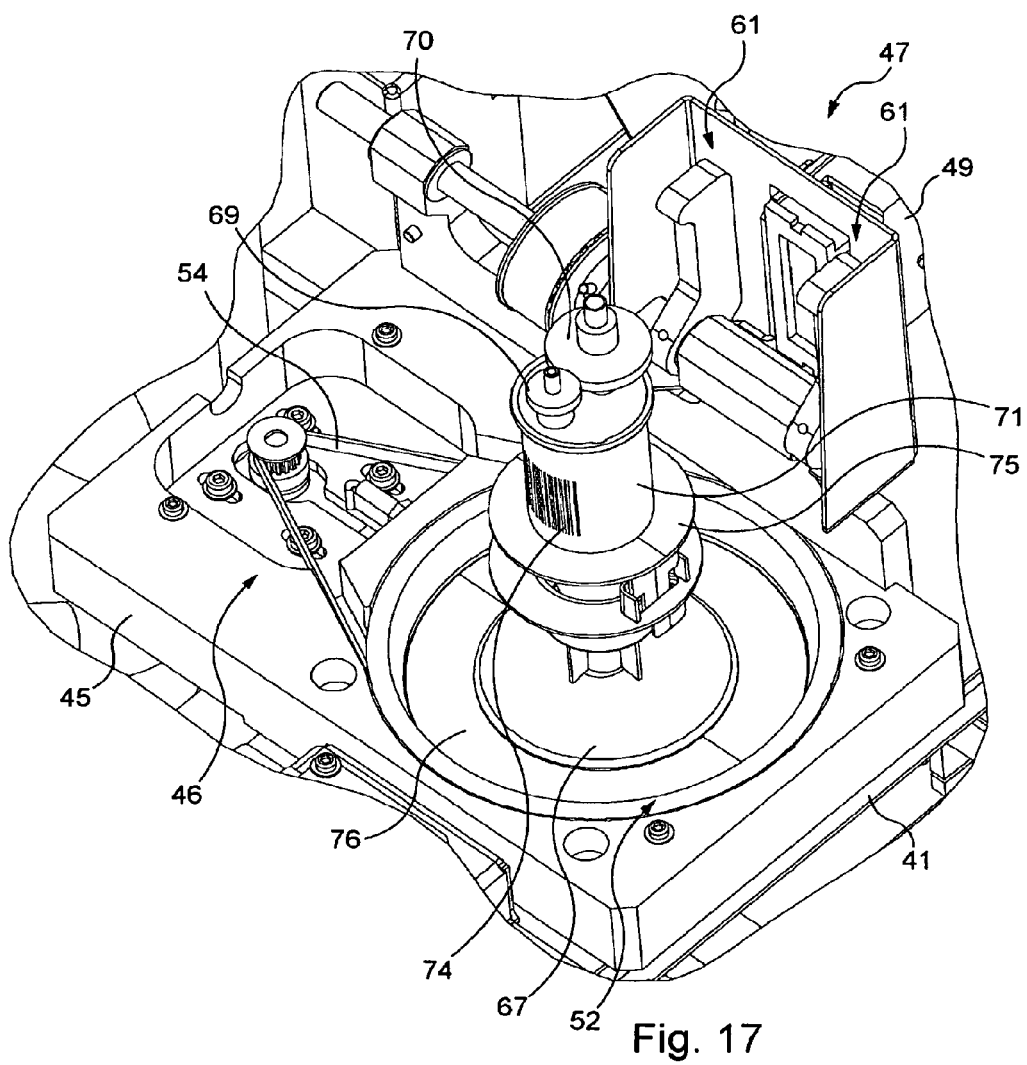
Figure 18:
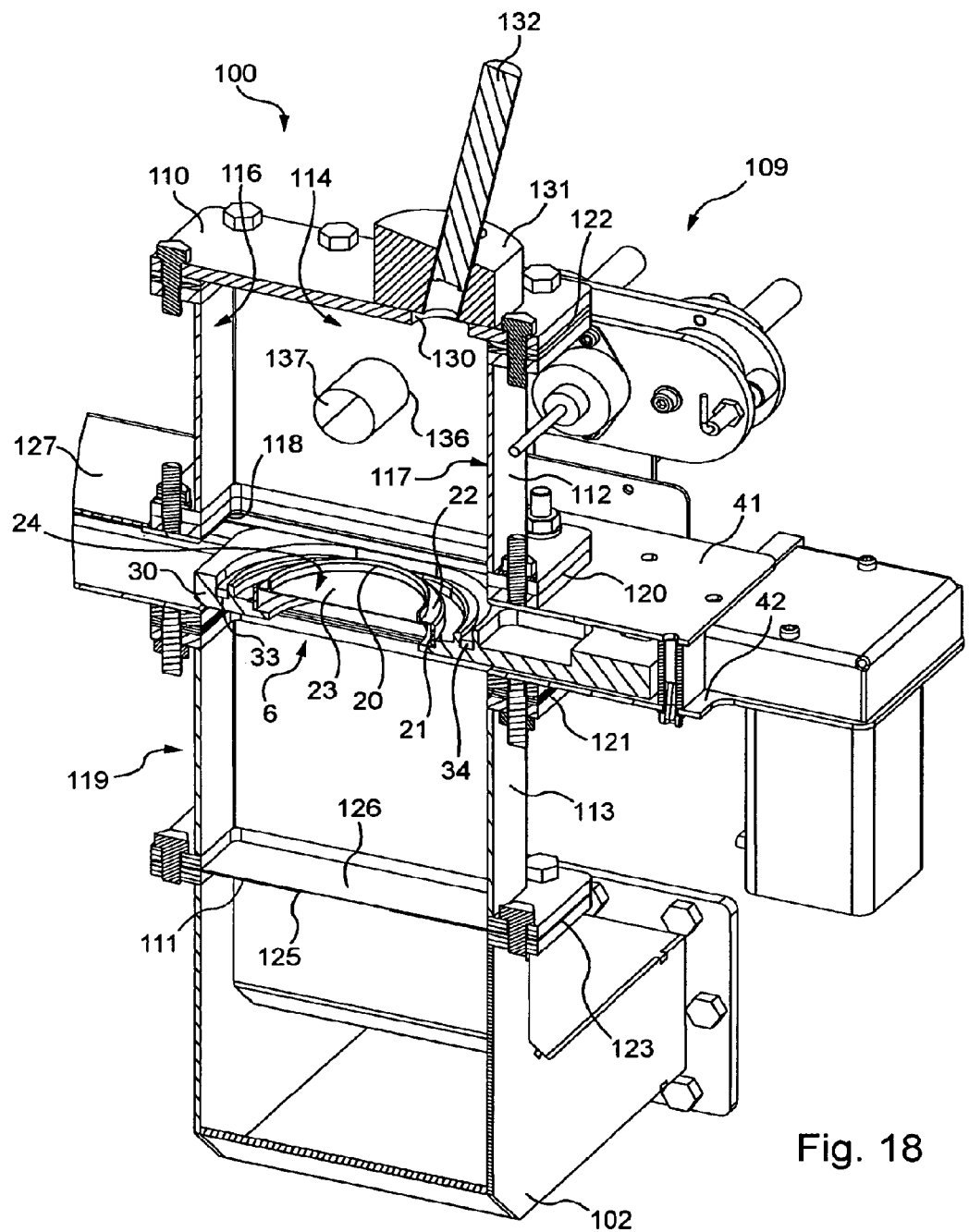
Figure 19:
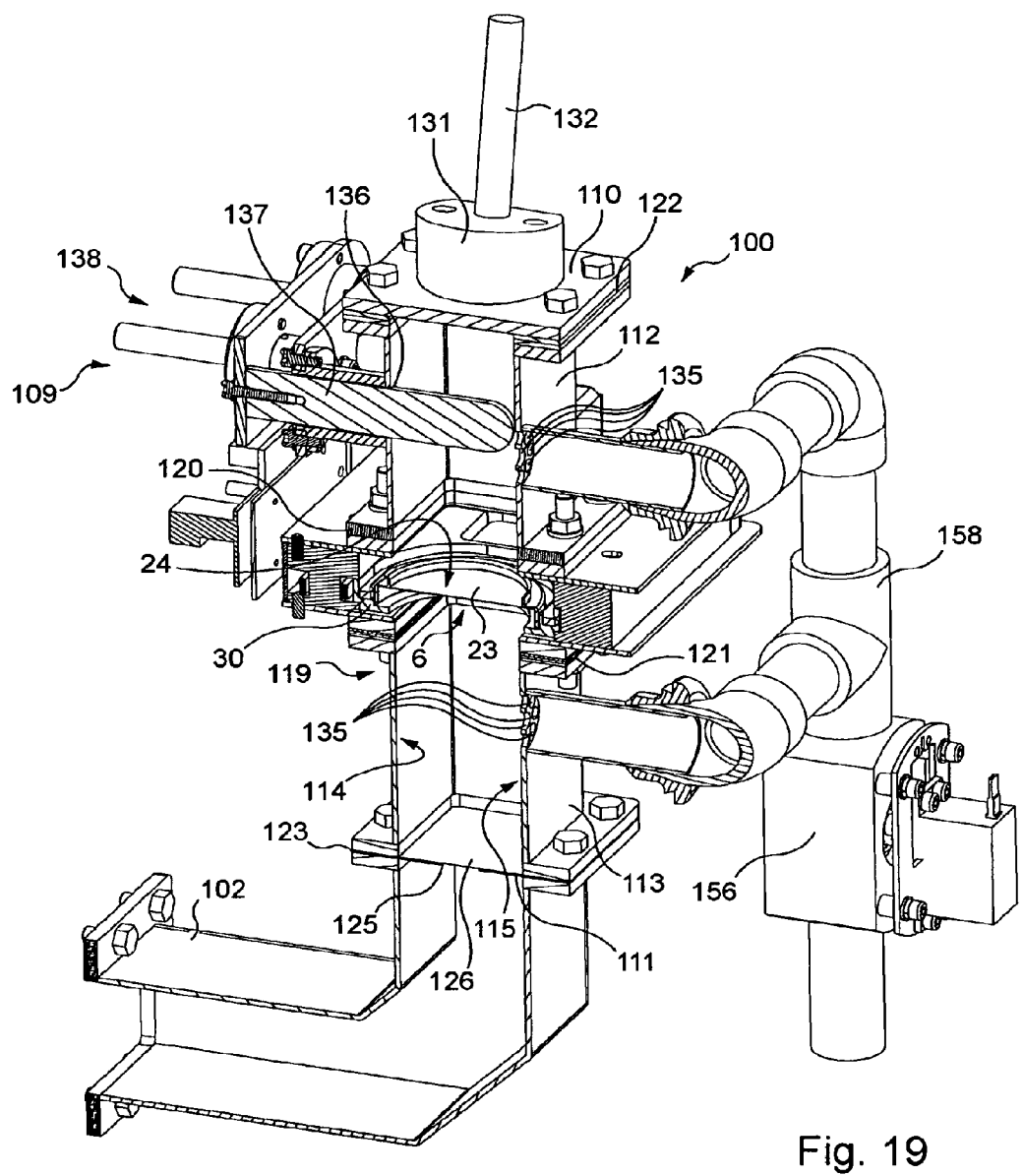
Figure 20:
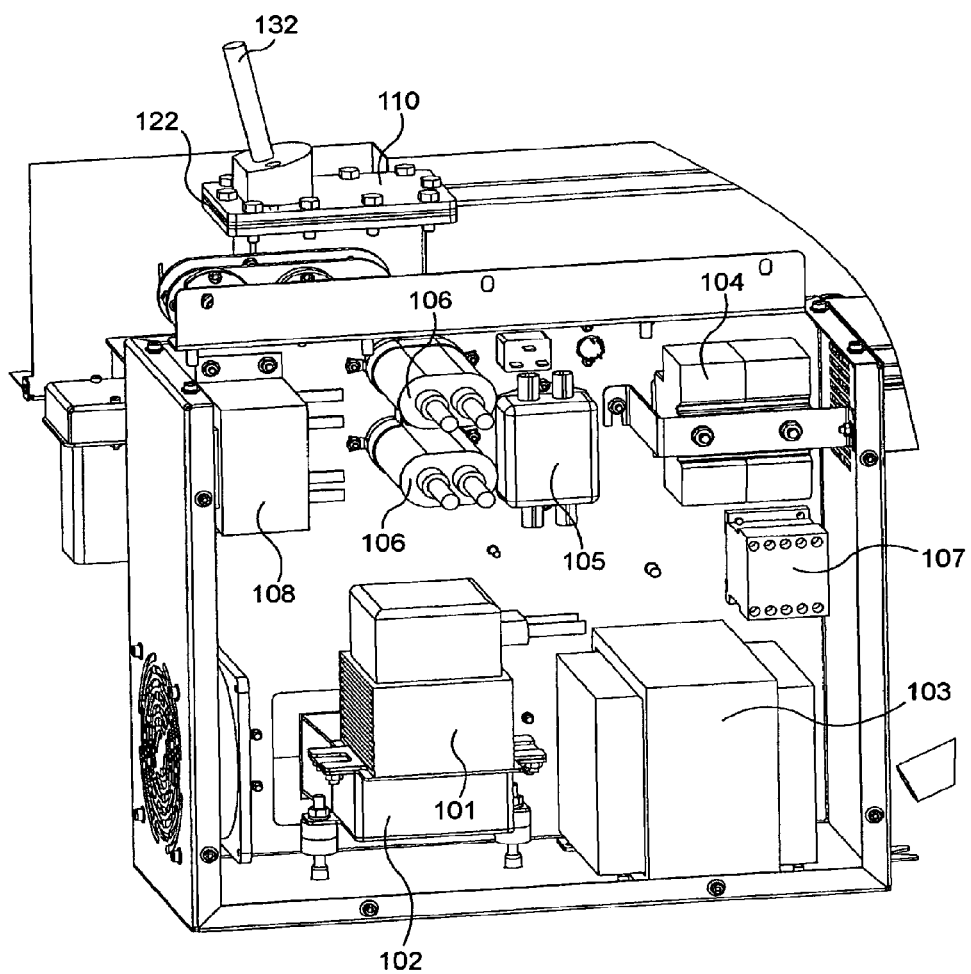
Figure 24:
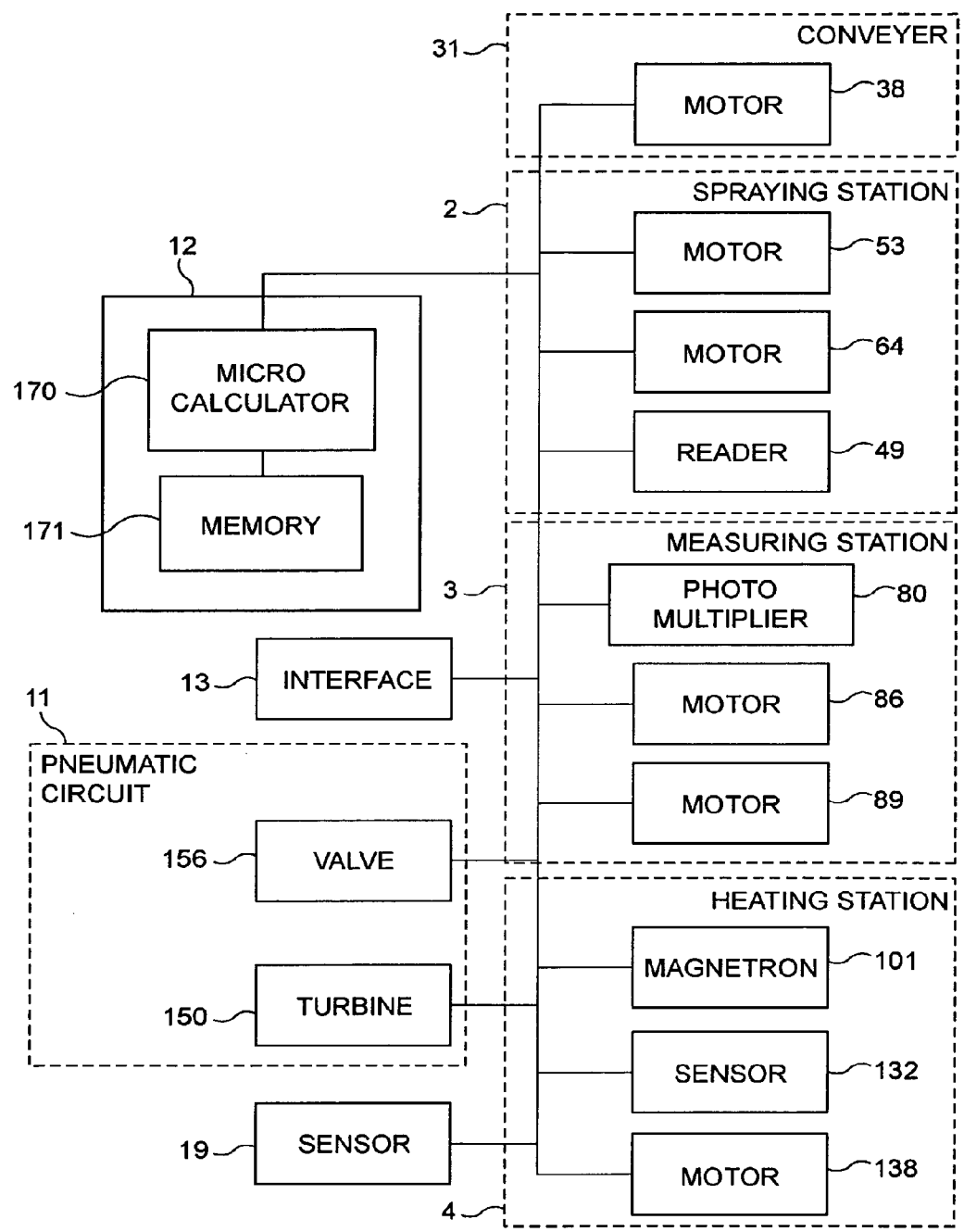

FIG. 12 is a similar view to FIG. 10 but in a position in which the members for protection against the light of the measuring station have been moved to isolate the filter unit from the light;

FIGS. 13 and 14 are two partial enlarged views of the spraying station illustrating an actuator of the spraying device represented respectively in a position in which the arms of the actuator are away from the device and in a position in which those arms are in contact with the device;

FIG. 15 is a similar view to FIG. 14 but in elevation-section and FIG. 16 is a similar view to FIG. 15 but representing the arms of the actuator in their positioning for actuation of a pump of the device to emit a jet of droplets;

FIG. 17 is a similar view to FIG. 13 but representing the device and the receptacle for receiving that device after having turned them through a half turn;

FIGS. 18 and 19 are two views respectively similar to FIG. 3 and FIG. 4 but showing in isolation and enlarged the microwave cavity of the heating station with two different cross-sectional planes;

FIG. 20 is a perspective view of the machine from the side which can be seen to the right in FIG. 2;

FIGS. 21 and 22 are both diagrammatic views of the microwave cavity respectively illustrating the position that the filter unit occupies in the cavity on heating and the distribution of the lines of current of that cavity;

FIG. 23 is a diagrammatic representation in section of that cavity along the plane XXIII indicated in FIG. 21 and illustrating the amplitude of an electromagnetic field in the case of a resonating regime of stationary waves setting up in the microwave cavity; and FIG. 24 is a diagrammatic representation of a logic control unit which that machine comprises and different elements of the machine that it commands and/or from which it receives data.

The machine 1 illustrated in FIGS. 1 to 12 comprises a spraying station 2, a station for measuring luminescence 3 and a heating station 4 disposed one after the other and a conveyor duct 5 for a filter unit 6 to pass the unit from one station to the other.

Figure 1:
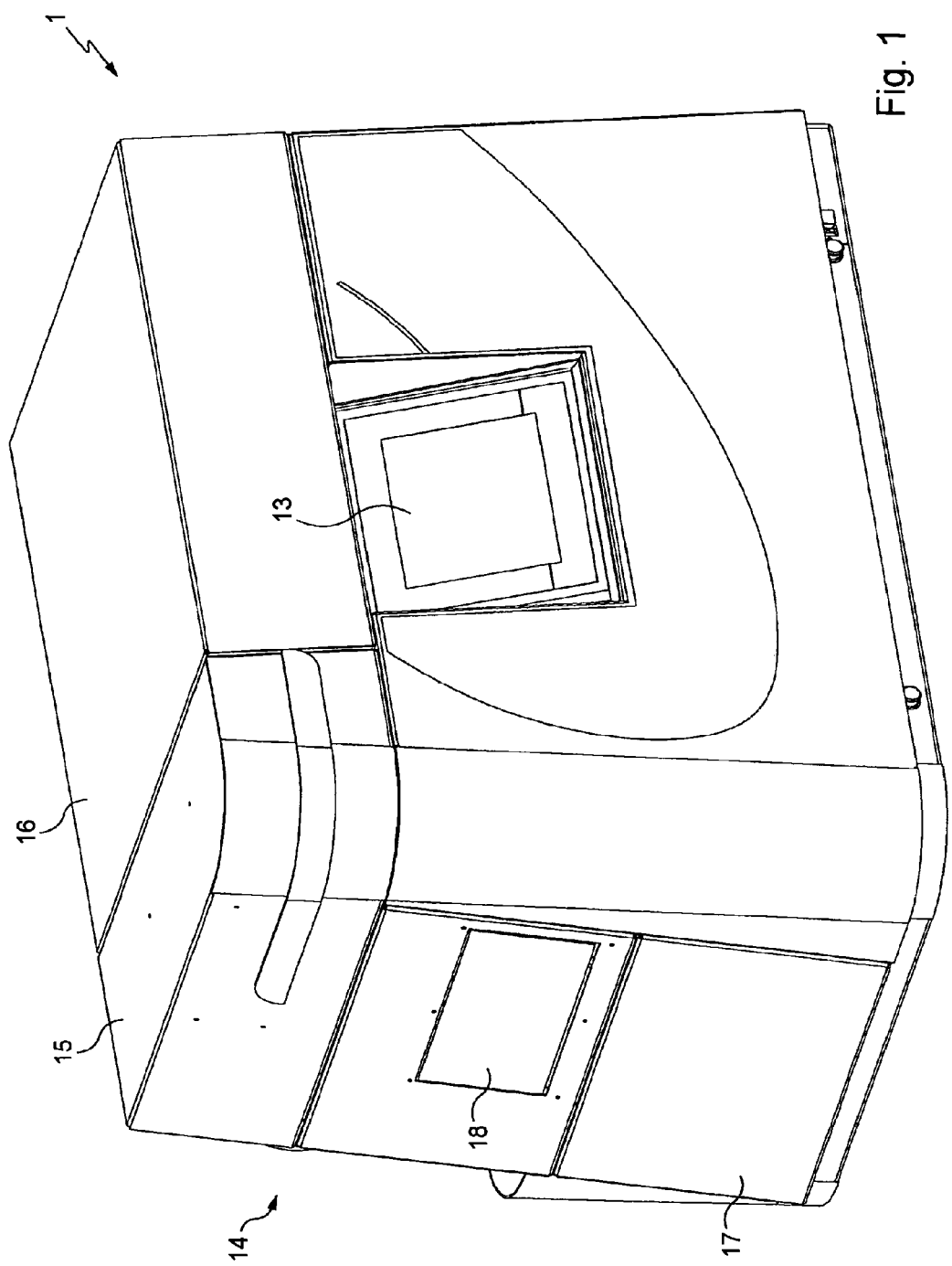
FIG. 1 is a perspective view in accordance with the invention.

The machine 1 also comprises a conveyor 10 (FIG. 15) for that unit in the duct, a pneumatic circuit 11 (FIG. 6) associated with that duct, a logic control unit 12 (FIG. 24), a user interface 13 and a casing 14 protecting all of these items (FIG. 1).

The casing 14 in FIG. 1 has three removable access doors 15, 16 and 17 and an obturation cover 18 of the conveyor duct.

In the illustrated example, this machine is provided for analyzing filter units such as the unit 6 shown enlarged in FIG. 18 and having a first tubular portion 20, a second tubular portion 21, a junction wall 22 of those portions and a microporous membrane 23 at that wall 22. The membrane 23 is adapted to retain microorganisms at a step of filtering a liquid or a gas through the membrane or else by contacting a solid with that membrane.

The conveyor 10 of the machine illustrated in particular in FIGS. 15 and 16 comprises a shuttle 30, moveable in the conveyor duct 5 as well as a conveyor mechanism 31 for that shuttle.

The shuttle 30, provided to receive a filter unit 6 has a collar 35 and a circular aperture 32 as well as an annular groove 33 surrounding that aperture and in which a seal 34 against the light is received.

The conveyor mechanism 31 comprises two belts 36, a set of toothed wheels 37 at each end of the duct and a motor 38 to turn the wheels and drive the movement of the belts and the shuttle.

Figure 11:
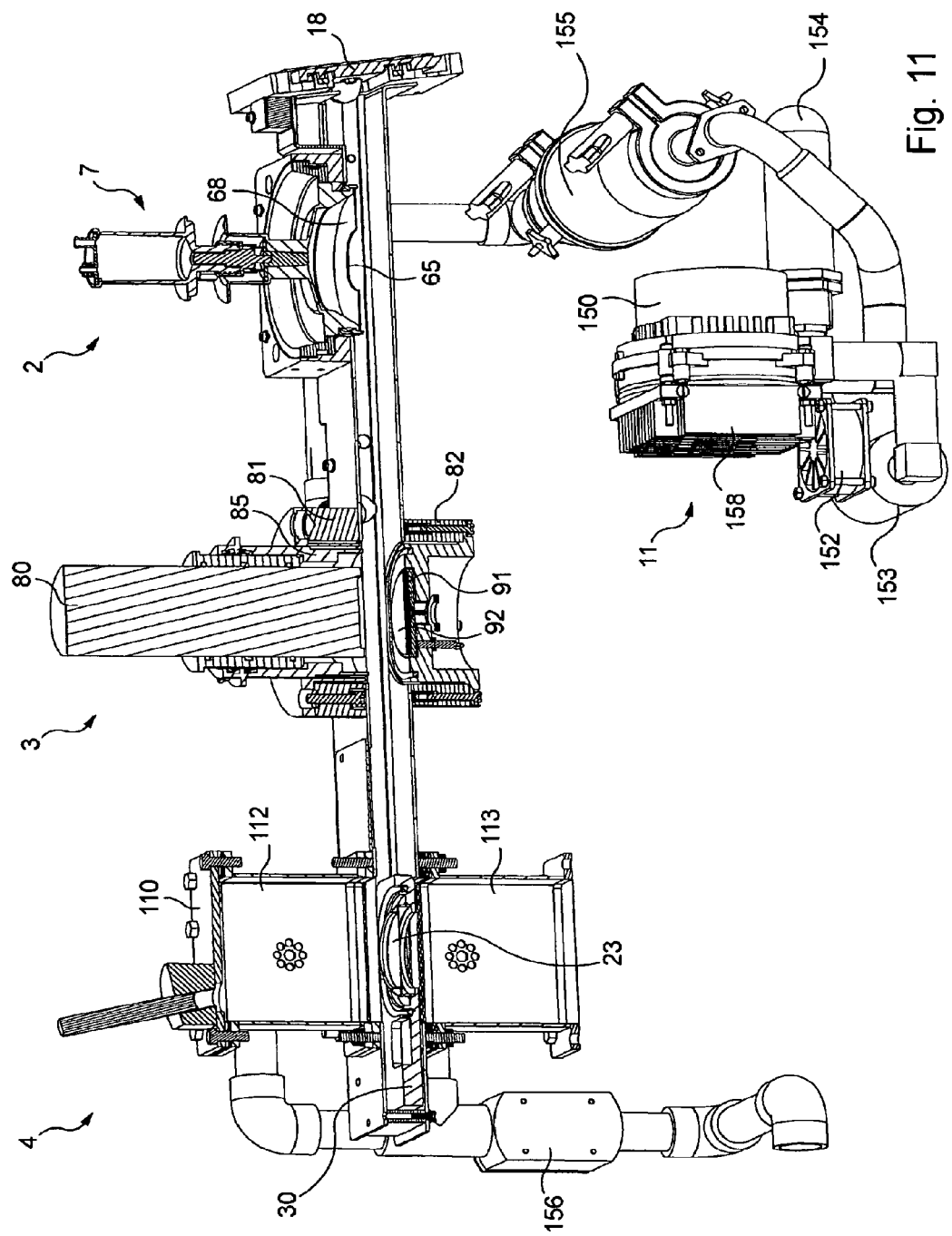

The shuttle 30 is attached by its edges to the belts 36 and is thus rendered mobile between a receiving position (FIG. 8) in which the shuttle projects from the duct of the machine, a spraying position (FIG. 9) situated under the spraying station, a measuring position under the measuring station (FIG. 10), and a heating position (FIG. 11).

The duct 5 illustrated in FIG. 5 is delimited by two plates 41 and 42 disposed parallel to each other and connected together by a rectangular flange 43 closing the duct around its whole periphery except at the end that can be seen to the left in FIG. 2 in which the latter has a window 40 by which passes the shuttle to occupy its position for receiving a filter unit 6.

The cover 18 of the casing 14 obturates that window 40 when the shuttle 30 is not in its receiving position by virtue of a spring (not visible) which enables that cover 18 to close by elastic return action onto that window in the absence of the shuttle.

The spraying station 2 illustrated in FIGS. 13 to 17 comprises a base 45 fixed to the plate 41, a rotary cradle 46 adapted to receive a spraying device 7, an actuator 47 for that device, a protective skirt 48 (FIG. 2) surrounding the cradle and a barcode reader 49.

The cradle 46 comprises a receiving receptacle 52 received in a housing of the base 45, a motor 53 (FIG. 3) and a belt 54.

The receptacle 52 has a substantially cylindrical portion 55 (FIG. 15) with the internal surface 56 being flared as well as an annular edge 57 projecting inwardly of the portion 55 at the end of that portion that is the closest to the duct 5. In portion 55 there is provided an annular groove 58.

The belt 54 is connected to the shaft of the motor and is received in the groove 58 of the receptacle 52 to turn it when the motor operates.

The actuator 47 comprises two moveable arms 61 acting on the device 7 to enable the ejection of droplets of reagent on the membrane 23 of the filter unit 6, as well as a stepper motor 64 (FIG. 15) and a belt 60 adapted to rotationally move the moveable actuating arms. Each arm comprises a central body 62 at the end of which is attached an actuating finger 63 which comes to bear against the device.

The receptacle 52 is provided to receive a spraying device 7 chosen from a plurality of spraying devices all of the same type.

In the example illustrated, such a device comprises an annulus 66, a spraying bell 67, an absorbent pad 68 (FIG. 8), a reservoir 71, a nozzle 72, a pump 73 and an item of identification 74.

The pad 68 is disposed between the bell 67 and the annulus 66, the pad having an opening 65 at its center.

The reservoir 71 communicates with the exterior through an air filter 69 forming a vent and a liquid filter 70 (in order to be able re-use the device by refilling it with reagent by that filter)

The reservoir 71 has a bearing collar 75 and the bell 67 a bearing collar 76.

In the example illustrated the reservoir 71 contains a reagent revealing the presence of ATP by luminescence.

The pump 73 has an inlet aperture 77 issuing into the reservoir 71 and a delivery aperture 78 issuing into the nozzle 72 and is adapted to be actuated by the reservoir 71 and the nozzle 72 (FIG. 16) moving towards each other in order to emit from that nozzle the jet of droplets.

The item of identification 74 (FIGS. 15 and 16) is here a self-adhesive label bonded to the wall of the reservoir 71 and bearing barcode markings.

The reader 49 is disposed so as to be turned towards the reservoir 71.

The measuring station 3 illustrated in FIGS. 2 to 12 comprises a photomultiplier 80, a base 81 and a base 82 on each side of the duct, an obturating device 83 situated on the photomultiplier side and an obturating device 84 situated on the opposite side from the photomultiplier.

The obturating device 83 has a cylindrical obturating collar 85 between the base 81 and the photomultiplier 80 as well as a mechanism 86 for translational movement of that collar parallel to the photomultiplier comprising a motor and a set of pulleys and belts to enable that movement.

The obturating device 84 comprises a piston 88 and a motor 89 adapted to impart translational movement to the piston. The piston comprises a head 90, a shaft 91 and a foam disc 92 bonded to the piston head (FIG. 3).

The heating station 4 illustrated in FIGS. 18 to 20 comprises a microwave cavity 100 of parallelepiped general shape, a magnetron 101, and a wave guide 102 connecting the cavity to the magnetron, as well as a device 109 for adjusting the resonant mode of the cavity.

The cavity 100 and the duct 5 form a treatment enclosure.

The heating station 4, for the proper operation of the magnetron 101 and as illustrated in FIG. 20, comprises a high voltage transformer 103, a circuit breaker 104, a series filter 105, a high voltage rectification circuit 106, contactors 107 and a transformer 108 for heating the filament of the magnetron.

The cavity 100 comprises two members 110 and 111 that are reflective of electromagnetic waves, an upper body 112 and a lower body 113 together delimiting a guide 119 of rectangular cross-section extending between said reflective members, the guide 119 having two large internal surfaces 114 and 115 along the large sides of the cross-section and two small internal surfaces 116 and 117 along the small sides of the cross-section.

At the conveyor duct the internal surface 116 has a window 118 of rectangular outline enabling passage of the shuttle 30.

The body 112 (respectively 113) is fixed to the duct via a flange 120 (respectively 121) and is fixed to the reflective member 110 (respectively 111) via a flange 122 (respectively 123).

The reflective member 111 is formed from a plate provided with a central rectangular opening 125 termed iris and covered by a plastics material 126 (here Mylar®).

At the duct situated between the photomultiplier 80 and the cavity 100, at the same level as the flanges 120 and 121, these latter are extended by plates 127 disposed against the plates 40 and 41 of the duct in order to minimize wave leakage.

In the reflective member 110 there is provided an aperture 130 around which is fixed a base 131 in which is received an infrared sensor 132 slightly inclined and pointed towards the center of that cavity.

The upper 112 and lower body 113 each have, at the side where surface 115 is, a series of apertures 135 neighboring each other such that the cavity 100 communicates with the moisture evacuation pipes of the pneumatic circuit 11 without giving rise to too much wave leakage.

In the upper body 112 there is also formed an aperture 136, at the side where surface 114 is.

The device 109 comprises an obstacle 137 of teflon of cylindrical general shape passing through the upper body 112 by the aperture 136 as well as a mechanism for translational movement 138 (provided with a motor and a set of pulleys) transversely to surfaces 114 and 115 so as to be able to vary the volume of teflon present within the cavity 100 by translational movement.

The magnetron 101 is provided to emit a traveling wave at a frequency of 2.45 GHz guided via the wave guide 102 into the cavity, the wave entering the cavity 100 through the iris 125.

The traveling wave reflects against the reflective members 110 and 111 such that it sets up a resonant stationary wave regime within the cavity 100 with the electric field presenting field lines parallel to the small surfaces 116, 117 of the enclosure. This resonant field presents a succession of amplitude nodes and antinodes as illustrated diagrammatically in FIG. 23. As will be seen below, when the item to heat is situated at an amplitude antinode, this regime makes it possible to heat that item extremely efficiently and rapidly.

The machine also has an ultrasound sensor 19 (represented diagrammatically in FIG. 24) making it possible, by sending ultrasound waves towards the shuttle 30 in its reception position and analyzing the reflected wave transmitted by that sensor to the logic control unit 12, to ensure that the filter unit 6 deposited on the shuttle in the reception position really matches the type of one of the types of unit intended to be analyzed by the machine, the sensor transmitting to the control unit 12 an arrangement parameter of the filter unit 6 to verify (such as its height or its outer diameter, its spatial conformation, etc) and making it possible to recognize its type.

For each machine, in the case in which the machines are provided for a single type of filter unit, the position of the obstacle 137 is fixed in advance (after trials in the factory, with the help of a network analyzer so as to establish the resonant regime in the cavity 100 in the presence of a filter unit 6).

The sensor 19 then makes it possible to ensure that the arrangement criterion associated with the type of support to analyze is satisfied, that is to say that it is in fact a unit 6 of the type intended to be analyzed which is disposed on the shuttle 30 in its reception position.

This sensor supplies the value of the height of the filter unit 6 to the control unit 12, that unit 12 verifying whether that height is in fact that of the units intended to be analyzed with a possible difference of a margin of error due to the dimensional variations from one unit to another.

If that height belongs to a value range set in advance (for example [11 mm; 13 mm] for a unit which is 12 mm high) then the control unit 12 commands the start of a cycle and if that height is not in conformity (outside the range) then the control unit 12 refuses to start an analysis cycle and warns the operator (who may for example have put in place a filter unit which is not of the type intended to be analyzed by the machine or have forgotten to remove the cover of that unit, which case is also detected by the sensor 12 on account of the difference in height of a unit with and without its cover).

When the machine is intended for analyzing supports of different types, that is to say of different dimensions and structures, there is associated with each type of support a specific recognition criterion (for example belonging to a predetermined value range) and a predetermined position of the obstacle 138, recorded originally in the memory 171 (after determination in the factory of those positions by virtue of the network analyzer).

For each new filter unit 6 to analyze, the control unit 12 thus recognizes, on the basis of the arrangement parameter transmitted by the sensor 19, the type of the support introduced into the machine and commands the means 138 for movement in order to make the obstacle 137 take the predetermined position in the cavity 100 recorded in the memory 171 associated with the recognized type of support.

More particularly, the resonant regime is sensitive to numerous sources of instability, and in particular to the introduction of items into the cavity 100 such as a unit 6, and the obstacle 137 enables a fine adjustment of the cavity 100 in order to optimize the conditions for obtaining that regime in the presence of a unit 6 in the cavity.

The pneumatic circuit 11 illustrated in FIGS. 6 to 12 comprises a turbine with blades 150 having an air inlet aperture and an outlet aperture, a Peltier effect thermoregulation device 151 disposed against the turbine, a cooling fan 152 for the thermoregulation system, a silencer 153, an air filter 154, a microbiological filter 155 and a valve 156.

The air filter 154 is connected by a pipe to the silencer 153 itself connected to the inlet aperture of the turbine 150, the outlet aperture thereof being connected to the microbiological filter 155 itself connected to the conveyor duct 5 for the shuttle 30 by issuing via a pipe into that conveyor duct at an aperture 157 (FIG. 8) formed in the lateral flange 43 of the conveyor duct and situated between the measuring station 3 and the spraying station 2, in the neighborhood of the measuring station.

The thermoregulation device 151 juxtaposed against the turbine makes it possible to obtain thermoregulated air (at substantially constant temperature) within the conveyor duct, the device itself being cooled by the fan 152 disposed close to a cooling radiator of the device.

The pneumatic circuit 11 continues beyond the microwave cavity 100 by an evacuation flue 159 formed from two pipes communicating with the interior of the cavity via orifices 135, those pipes joining together at a T-connection 158 so as to attain the inlet aperture of the valve 156, the outlet aperture of that valve issuing by virtue of a pipe to which it is connected externally of the enclosure.

The filters 153 and 154 are arranged so that they can be easily replaced by an operator who obtains access thereto by opening the door 17.

The user interface 13 has a touch screen connected to the control unit 12 to enable the user to read information, to give instructions or to parameterize the machine, launch a cycle, etc.

As illustrated in FIG. 24, the different actuating motors, the photomultiplier, the magnetron, the user interface, the different processing stations as well as the different sensors are connected to the logic control unit 12, this unit comprising a microcalculator 170 and an associated memory 171.

Several sensors other than those described above are disposed at the different processing stations and connected to the unit 12 to check the state of operation of the device, in particular a sensor for detecting the opening of the cover 18 beside the spraying device 7 and several shuttle position sensors.

The unit 12 is adapted in particular to manage the instructions for launching or stopping an analysis cycle, to receive instructions from the operator coming from the interface 13 or to record in the memory the data coming from the photomultiplier, from the bar code reader or from the motor of the actuator for example.

The operation of the machine will now be described.

Two preliminary operations must be carried out by the machine, i.e. a decontamination operation to disinfect the enclosure in which the shuttle 30 is conveyed and an operation of calibrating the actuator to obtain optimal spraying of the spraying device 7 which was placed in the receptacle.

In the decontaminating step, the operator grasps a conventional filter unit 6 on the membrane from which he deposits a volume of liquid biocidal agent, for example 500 microliters of hydrogen peroxide (H.sub.20.sub.2) at 35% concentration, that volume being absorbed by the membrane.

That filter unit 6 is then placed on the shuttle 30 then in its reception position and is brought at design speed to the microwave cavity 100. The magnetron 101 is controlled by the unit 12 to establish within that cavity the regime of resonant stationary waves described above in order to heat the liquid peroxide to vaporize it in the microwave cavity.

Once this heating step has been carried out, the shuttle 30 is moved at slow speed (approximately 8% of the design speed) within the duct 5 towards the spraying station 2 to enable the hydrogen peroxide vapors to spread within the whole duct 5 and thus destroy the germs which could be present on its surface. Once the shuttle has arrived under the spraying device 7, the gaseous peroxide is left to act for fifteen minutes then the return of that shuttle is commanded at design speed to the cavity 100 to perform a second cycle of the same type (heating then movement of the shuttle at slow speed to the spraying device and action of the gas).

Once these two cycles have been carried out, the valve 156 is opened and the turbine 151 of the pneumatic circuit is commanded to blow in order to dry and inactivate the vaporized hydrogen peroxide and in order to evacuate it.

The electronic boards disposed within the machine are placed in such a manner as to avoid premature oxidation of the electronic circuits by the hydrogen peroxide.

The other prior step consists of calibrating the actuator 47 of the spraying station 2 to determine for each spraying device 7 the optimal end of travel angular position of the arms 61 of the actuator against the device 7 which was placed in the cradle 46 in order to obtain the best possible spray.

More particularly, the variations in the dimensions of the devices on molding of the consumables means that it is necessary to perform this calibrating step for each device 7.

In a first phase, the operator starts by loading a device 7 into the machine. For this he opens the door 15 in order to place a spraying device 7, chosen from the plurality of identical devices, in the receptacle 52 of the rotary cradle 46, the collar 76 of that device coming to bear against the border 57 of the receptacle.

The reader 49 is then commanded by the unit 12 to read the label 74 present on the reservoir 71 of the device if need by commanding the rotation of the receptacle 52 in order to turn the device to place the bar codes of the label 74 facing the reader (FIG. 15).

If the data thus transmitted by the reader to the control unit 12 are not already recorded in the memory of the unit (new consumable), the unit starts a new calibration phase for that device which it does not have in memory. It records, in the memory 171, the identification data of that new consumable read by the reader 49 on the label 74 and commands the motor 64 to drive the arms 61 in rotation at a slow speed (less than the design actuating speed of the devices) until they come into contact with the consumable at the collar 75. In parallel the unit 12 receives from the motor 64 and processes a parameter representing the force exerted by the arms on the device, here the current consumed by the motor, as well as a parameter representing the angular position of those arms, here a number of motor steps.

The unit 12 controls the motor until the measured force parameter attains a predetermined threshold corresponding to the force necessary to actuate the pump of that device, that is to say to bring the reservoir 71 and the nozzle 72 towards each other (as illustrated in FIG. 16). When that parameter reaches that threshold, the unit records in its memory the position parameter of the arms (as a number of motor steps) and commands the lifting of the arms of the actuator.

By virtue of the calibrating step, the control unit 12 associates, for a given bar code, an optimal end of travel position of the arms of the actuator.

The liquid sprayed during this phase is recovered in a cup placed beforehand by the user in the shuttle 30 which is then placed under the spraying station 2.

If the device 7 is already known to the unit 12 (consumable already calibrated), it will search in its memory for the angular value of end of travel position of the arms associated with that consumable without having to perform the above steps again.

The machine is now ready starting from that time to perform a complete cycle of analysis of a filter unit 6 which will be described below, the control unit 12 awaiting the instructions from the operator.

In the absence of instructions from the operator, the valve 156 and the cover 18 are closed and the turbine 150 is then commanded by the unit 12 to operate according to a first mode directed to maintaining a slight pressurization (about twenty pascals above atmospheric pressure, as for clean rooms) so as to avoid the introduction of dust or germs into the duct 5 and into the cavity 100.

In this mode of operation, the cover and the valve are closed such that the throughput of the turbine 150 is deliberately chosen to be low and just sufficient to compensate for the slight leakages that may be present along the duct 5 and the cavity 100.

When the operator wishes to perform a cycle, he indicates this to the unit 12 via the touch screen of the interface 13.

The unit 12 then commands the movement of the shuttle 30 to its reception position, projecting from the window 40. During its movement, the shuttle comes into contact with the cover 18 and drives the opening of that cover at a time t.sub.1.

From that time t.sub.1 and for as long as the cover 18 is open, the turbine 150 is commanded to operate according to a second operating mode in which it blows a throughput of air giving rise to a laminar flow of that air in the direction going from the aperture 157 to the window 40 of the machine so as to avoid germs being able to enter by that window while the cover is open.

The operator then places the filter unit 6 to analyze on the movable shuttle 30.

By virtue of the ultrasound sensor 19, and as set out earlier, the machine then detects that the filter unit 6 has in fact been deposited on the shuttle 30 and that the dimensions of the unit do in fact conform to those intended for being analyzed.

If the consumable is in conformity, the unit 12 then commands the motor 38 actuating the bands 36 so as to move the shuttle 30 from its reception position to its measuring position, under the measuring station 3.

During this movement, when the shuttle 30 has entirely passed through the window 40, the cover 18 of the machine 1 closes by elastic return action in order for the following steps to be performed in a closed environment.

When the cover 18 has closed by withdrawal of the shuttle 30 at a time t.sub.2, the turbine 150 is then commanded by the control unit 12 to operate according to the first mode described above and directed to maintaining slight pressurization.

When the membrane 23 is placed under the measuring station 3, a first measurement of luminescence is carried out by the photomultiplier 80 to determine the natural fall-of in the phosphorescence emitted by the plastics material and the membrane 23 of the filter unit 6 (first curve for blank test).

The shuttle 30 is then commanded to return under the spraying device 2, the motor 64 is then commanded by the unit 12 to move the arms 61 to the position recorded beforehand during the calibrating phase, at a design speed for lowering the arms. The arms 61 are next held in position for a specific duration then are raised again at a design speed for raising the arms.

The end of travel position of the arms, the speed of lowering and raising, and the duration of holding in position are determined according to the characteristics of the pump 73 of the device 7 supplied by the manufacturer to ensure optimal actuation and re-priming of that pump so as to render the spray as homogenous and reproducible as possible.

It is also to be noted that the nozzle 72, the spraying bell 67, the absorbent pad 68 and the diameter of the opening 65 of that pad are intended to ensure that the spray is as homogenous as possible, that is to say adapted to let only the portion of the jet pass which is the most homogenous (the peripheral portion of the jet being trapped in the pad) while preventing droplets from bouncing off (these latter being absorbed by the pad). This selected portion of the jet thus deposits over the whole useful surface of the membrane.

The spraying by droplets makes it possible to sufficiently divide the deposited liquid to avoid any risk of dilution. Droplets is understood to mean drops that are sufficiently small for the jet thus sprayed to form a spray.

The reagent is thus contacted with the extraneous ATP present on the membrane not coming from the microorganisms that it holds but from external contaminations, for example on transportation or at the filtering step.

Putting the reagent in the presence of the extraneous ATP gives rise to a chemical reaction which generates light and which consumes the extraneous ATP. The extraneous ATP so consumed will not interfere with course of the following steps of the analysis cycle. The reagent will not interact with the ATP of the microorganisms, as, at this stage of the cycle, the latter is still protected from the reagent by the envelopes of the microorganisms.

So as to optimize the homogeneity of the deposit of droplets, the motor 53 is commanded to drive the belt 54 and thus turn the receptacle 52 through a half turn (180.degree.) in its plane and relative to its center, in the general direction of spraying going from the device 7 towards the unit 6, the shuttle 30 remaining immobile and under the receptacle 52 during this rotation. In this manner, the receptacle 52 and the shuttle 30 come into a different relative angular position from that which they occupied before the rotation of the receptacle 52. The unit 12 then commands the arms 61 of the actuator 47 a second time to perform a second spraying operation of a jet of droplets on the membrane.

The shuttle 30 is then once again placed under the photomultiplier 80 so as to establish a second reference curve for measuring the luminescence coming from the contacting of the reagent and the extraneous ATP (second curve for blank test).

The shuttle 30 is next moved to a predetermined location in the microwave cavity 100, at an amplitude antinode to heat the membrane 23, with the planar surface 24 of that membrane being perpendicular to the large surfaces 114, 115 and to the small surfaces 116, 117 of the guide 119 (FIGS. 18, 19 and 21).

For this and as stated previously the unit 12 commands the magnetron 101 at a time $t_3$ such that the resonant regime establishes in the cavity 100, the unit 12 then, starting at that time, commanding the opening of the valve 156 of the pneumatic circuit 11 and the operation of the turbine 150 according to yet a third mode providing a maximum throughput in order, during the heating of the membrane 23, to evacuate the stagnant moisture in the cavity 100 generated by the evaporation of the water contained in the membrane and which could not only perturb the resonant mode of the cavity but also condense along the walls of that cavity.

The conveyor 10 and the cavity 100 are arranged to allow the shuttle 30 to be disposed in the cavity at a position in which the membrane 23 occupies an optimal predetermined location for the implementation of the heating of that membrane, that is to say and as illustrated in FIGS. 21 and 23 parallel to the lines of electric field, at an amplitude antinode and perpendicularly to the large and small surfaces of the guide (FIGS. 21 and 23).

It is also to be noted, as illustrated in FIG. 22, that the opening 118 is disposed so as not to give rise to cutting of the lines of current 140 of the cavity so as to minimize as much as possible the perturbations, generated by that opening for passage of the shuttle, to the resonant regime.

In this manner, when the resonant regime is established in the cavity 100, it enables very fast heating of the membrane 23 to be obtained, which reaches a temperature of approximately 100.degree. C. in a few seconds.

The unit 12 commands the magnetron 101 in order for the temperature of surface 24 of the membrane measured by the infrared sensor 132 and transmitted to the unit 12 to reach the temperature setting (here 100C) and for it to be regulated around that value. The sensor is thus oriented so as to measure the temperature of the center of the upper surface of the membrane of the filter unit 6 without being hindered by the teflon obstacle 137. As the thickness of membrane 23 is very small the temperature measured at its surface substantially corresponds to the temperature within it, such that the membrane is heated relatively evenly. This membrane is also disposed such that the resonant regime (at the wavelength of the stationary wave) makes it possible to heat the membrane evenly over the whole of its surface.

During the rise in temperature up to the temperature setting, the reagent deposited beforehand is eliminated by that heating before the lysis of the microorganisms has begun such that there is no interaction between that reagent and the ATP of the microorganisms since at the time at which the lysis of the microorganisms occurs all the reagent has already been eliminated by the heating of the membrane.

The envelope of the majority of the microorganisms is thus only destroyed (and the ATP of the microorganisms thus rendered accessible) once the reagent deposited beforehand has been eliminated such that the major portion of the ATP of the microorganisms is not consumed by that reagent.

Furthermore, the elimination of the reagent is accelerated by the fact that the rise in temperature gives rise to a partial drying of the membrane rendering the heating more effective in eliminating the reagent.

The heating by microwaves makes it possible to provide only the quantity of energy necessary dosed on the basis of the quantity of water present on the membrane without producing residual heat that could perturb the following steps of the method.

Furthermore, the microwave power absorbed by the membrane is proportional to the volume of water to heat, such that the power absorbed by the membrane is in a way self regulated, that power being distributed naturally in the majority in the zones where the volume of water is greater.

After this heating step, the ATP of the microorganisms having undergone lysis is rendered accessible in order to be analyzed. The unit 12 commands the magnetron to stop at a time 4, the closing of the valve 156, and the return of the turbine 150 to the first mode.

As the analysis cycle takes place according to a time diagram established in advance, the times $t_0$ to $t_4$ are known to the unit 12 such that no sensor is necessary to command the change in operating mode of the turbine between $t_0$ to $t_4$ (the sensors present in the machine, in particular the sensor for opening of the cover 18, are uniquely there to ensure that the cycle proceeds properly).

It is to be noted that in the second and third operating modes of the turbine, even though a high throughput is sought, that turbine nevertheless remains capable of providing sufficient pressurization to pass through the filter 155 which has pores of very small diameter to retain the microorganisms, which gives rise to a high loss in pressure.

It is also to be noted that the aperture 157 issuing in the duct is sufficiently far from the window 40 (that is to say beyond a certain distance) to allow a laminar flow to establish at that window and also remains sufficiently far from the microwave cavity 100 not to draw into the laminar flow of air generated in the direction of the window 40, a portion of the residual moisture stagnating in that cavity (and thus minimize the risks of contamination).

The shuttle 30 is then moved in order to be again placed under the photomultiplier 80 so as to establish a new calibration curve (third curve for blank test) to determine the light emitted in response to the heating of the membrane.

The shuttle 30 is next placed under the spraying device 7 of the spraying station 2 in order to undergo there, as described previously, two successive spraying operations with a rotation of 180.degree. of the receptacle 52 between the two spraying operations, in the general direction of spraying, so as to obtain a deposit of reagent on the membrane that is as homogenous as possible.

The shuttle 30 is then again placed under the photomultiplier 80 to measure the luminescence coming this time from the contacting of the reagent with the ATP of the microorganisms.

At the time of each of these light measurements described above the obturating collar 85 is lowered as illustrated in FIG. 12 and becomes accommodated in the groove 33 of the shuttle against the "O"-ring seal 34 and the piston 88 is raised (the foam disc 92 of that piston coming into abutment against the shuttle 30) in order to completely isolate the photomultiplier 80 and the filter unit 6 from all extraneous light during the measurement by the photomultiplier 80.

The luminescence curve so obtained is compared to the different calibration curves (curves for blank tests) obtained beforehand in order to deduct therefrom the quantity of light emitted coming from the presence of microorganism ATP on the membrane. For this the unit 12 compares with each other in particular the amplitude and integral values of those curves, it thus being possible for the light emitted by the ATP of the microorganisms to be discriminated with respect to the light emitted by other phenomena (such as the natural fluorescence of the materials, the heating of the filter unit, or the residue of light due to the elimination of the extraneous ATP). It is thus possible to deduce thereby with great sensitivity the mass of ATP present on the membrane and coming from the microorganisms.

In a variant not illustrated, the container which receives the liquid hydrogen peroxide is not a filter unit 6 but any other type of container able to contain and/or absorb liquids.

In still another variant the shuttle 30 of the conveyor has a dedicated reception zone for the container diffusing the biocidal agent that is separate from the reception zone of the filter units 6.

The present invention is not limited to the embodiments described and represented but encompasses any variant form thereof.

The invention claimed is:

1. System for microbiological analysis of a support comprising:
   a container comprising a support and containing a biocidal agent;
   a machine for microbiological analysis comprising a treatment enclosure in which said support is received, at least two stations for treating said support, a conveyor comprising a shuttle which receives and moves said support, between said stations while said biocidal agent diffuses in said enclosure, as well as a pneumatic circuit comprising a turbine and a valve for evacuating said biocidal agent.

2. A system according to claim 1, further comprising a precursor agent of said biocidal agent in said container to activate to diffuse said biocidal agent, said machine also comprising means for activating said precursor agent.

3. A system according to claim 2 wherein said activating means comprise a station for heating said container.

4. A system according to claim 3 wherein the heating station comprises a microwave cavity and a magnetron.

5. A system according to claim 1, wherein said conveyor comprises a conveyor duct, and wherein said pneumatic circuit is in fluid communication with said duct.

* * * * *